United States Patent
Eriksen

(10) Patent No.: US 10,456,457 B2
(45) Date of Patent: Oct. 29, 2019

(54) PEPTIDE MIXTURE

(71) Applicant: TARGOVAX ASA, Oslo (NO)

(72) Inventor: Jon Amund Eriksen, Porsgrunn (NO)

(73) Assignee: TARGOVAX ASA, Oslo (NO)

(*) Notice: Subject to any disclaimer, the term of this patent is extended or adjusted under 35 U.S.C. 154(b) by 7 days.

(21) Appl. No.: 15/667,288

(22) Filed: Aug. 2, 2017

(65) Prior Publication Data

US 2017/0326218 A1 Nov. 16, 2017

Related U.S. Application Data

(62) Division of application No. 15/102,681, filed as application No. PCT/EP2014/077033 on Dec. 9, 2014, now Pat. No. 9,775,892.

(30) Foreign Application Priority Data

Dec. 9, 2013 (EP) .................................... 13196333

(51) Int. Cl.
| | | |
|---|---|---|
| *A61K 38/00* | (2006.01) | |
| *A61K 39/00* | (2006.01) | |
| *C07K 14/82* | (2006.01) | |
| *G01N 33/50* | (2006.01) | |
| *A61K 35/17* | (2015.01) | |
| *G01N 33/483* | (2006.01) | |

(52) U.S. Cl.
CPC .......... *A61K 39/0011* (2013.01); *A61K 35/17* (2013.01); *C07K 14/82* (2013.01); *G01N 33/483* (2013.01); *G01N 33/505* (2013.01); *A61K 2039/5158* (2013.01); *A61K 2039/57* (2013.01); *A61K 2039/70* (2013.01); *C12Q 2600/156* (2013.01); *G01N 2333/47* (2013.01)

(58) Field of Classification Search
CPC ..................................................... A61K 35/17
See application file for complete search history.

(56) References Cited

U.S. PATENT DOCUMENTS

| | | | |
|---|---|---|---|
| 9,757,439 B2 | 9/2017 | Eriksen et al. | |
| 9,775,892 B2 | 10/2017 | Eriksen | |
| 2009/0274714 A1 | 11/2009 | Singh et al. | |
| 2016/0331820 A1 | 11/2016 | Eriksen | |
| 2017/0189515 A1 | 7/2017 | Eriksen | |
| 2018/0021419 A1 | 1/2018 | Eriksen | |

FOREIGN PATENT DOCUMENTS

| | | | | |
|---|---|---|---|---|
| EA | 013466 B1 | 4/2010 | | |
| GB | 2328689 A | 3/1999 | | |
| WO | 1992/014756 A1 | 9/1992 | | |
| WO | WO-9214756 A1 * | 9/1992 | ......... | C07K 14/4746 |
| WO | WO 99/10382 | 3/1999 | | |
| WO | 2000/066153 A1 | 11/2000 | | |
| WO | 2014/0110408 A1 | 7/2014 | | |
| WO | 2015/0169804 A1 | 11/2015 | | |

OTHER PUBLICATIONS

Engelhard, Current Opinion in Immunology vol. 6 p. 13 (1994) (Year: 1994).*
Guo, et al Nature vol. 360 p. 384 (1992) (Year: 1992).*
Rammensee et al, Immunogenetics vol. 41 p. 178 (1995) (Year: 1995).*
Shastri et al J. Immunol. 1995 vol. 155 p. 4339 (Year: 1995).*
Gjertsen, M.K., et al., "HLA-A3 Restricted Mutant RAS Specific Cytotoxic T-Lymphocytes Induced by Vaccination with T-Helper Epitopes," J. Mol. Med., 81: 43-50 (2003).
Meyer, R.G., et al., "An Open-Label, Prospective Phase I/II Study Evaluating the Immunogenicity and Safety of a RAS Peptide Vaccine Plus GM-CSF in Patients with Non-Small Cell Lung Cancer," Lung Cancer, 58: 88-94 (2007).
Cox, A.D. et al., "Drugging the undruggable RAS: Mission Possible?" Nature Reviews, 13(11):828-851 (Nov. 2014). 24 pages.
Database Geneseq, "Human neuroblastoma RAS viral oncogene homolog (NRAS) mutant A146V," (Jul. 19, 2012). Two pages.
Douillard, J-Y. et al., "Panitumumab-FOLFOX4 Treatment and RAS Mutations in Colorectal Cancer," New England Journal of Medicine, 369(11):1023-1034 (Sep. 12, 2013). 12 pages.
International Search Report and Written Opinion of the International Searching Authority, dated Sep. 9, 2016, from International Application No. PCT/EP2016/063920, filed on Jun. 16, 2016. Eleven pages.
Negru, S. et al., "KRAS, NRAS and BRAF mutations in Greek and Romanian patients with colorectal cancer: a cohort study," BMJ Open 2014;4:e004652. doi:10.1136/bmjopen-2013-004652, (2014). Eight pages.
Sorich, M.J. et al., "Extended RAS mutations and anti-EGFR monoclonal antibody survival benefit in metastatic colorectal cancer: a meta-analysis of randomized, controlled trials," Annals of Oncology, 26:13-21 (2015). Thirteen pages.
Van Cutsem, E.V. et al., Fluorouracil, Leucovorin, and Irinotecan Plux Cetuximab Treatment and RAS Mutations in Colorectal Cancer, Journal of Clinical Oncology, http://co.ascopubs.org/cgi/doi/10.1200/JCO.2014.59.4812, (2015). Eleven pages.
Vaughn,C.P. et al., "Frequency of KRAS, BRAF, and NRAS Mutations in Colorectal Cancer," Genes, Chromosomes & Cancer, 50:307-312 (2011). Six pages.

(Continued)

*Primary Examiner* — Sheela J. Huff
(74) *Attorney, Agent, or Firm* — HoustonHogle LLP

(57) ABSTRACT

There is disclosed a peptide mixture suitable for eliciting an immune response. It comprises a first and a second peptide, each corresponding to a fragment of the RAS protein. Each of the first and second peptides comprises a region of at least 8 amino acids which includes position 13 of the RAS protein. Each of said regions of the first and second peptides independently has at least 6 amino acid residues, other than at said position 13, which are identical to the corresponding region of the RAS protein. Each of the first and the second peptides has a point mutation at the amino acid corresponding to said position 13. The point mutation of the first peptide is different from the point mutation of the second peptide.

6 Claims, 5 Drawing Sheets

Specification includes a Sequence Listing.

(56) References Cited

OTHER PUBLICATIONS

International Preliminary Report on Patentability, dated Dec. 28, 2017, from International Application No. PCT/EP2016/063920, filed on Jun. 16, 2016. Eight pages.
Abrams, S.I. et al., "Mutant ras epitopes as targets for cancer vaccines," MPSRCH GENBANK, Abstract (Feb. 1996). Two pages.
Altschul, S. et al., "Gapped BLAST and PSI-BLAST: a new generation of protein database search programs," Nucleic Acids Research, 25(17):3389-3402 (1997). Fourteen pages.
Applicant Response, dated Jan. 11, 2016, to Written Opinion of the International Preliminary Examining Authority for International Application No. PCT/EP2014/077033, filed on Dec. 9, 2014. Eight pages.
Bauer, C. et al., "Concomitant gemcitabine therapy negatively affects DC vaccine-induced CD8+ T-cell and B-cell responses but improves clinical efficacy in a murine pancreatic carcinoma model," Cancer Immunol Immunotherapy, 63:321-333 (2014). Thirteen pages.
Boon, T., "Toward a Genetic Analysis of Tumor Rejection Antigens," Advances in Cancer Research 58, 1992, pp. 177-210 Eighteen pages.
Conroy, T. et al., "FOLFIRINOX versus Gemcitabine for Metastatic Pancreatic Cancer," New England Journal of Medicine, 364(19):1817-1825 (2011). Ten pages.
Coulie, P.G. et al., "Tumour antigens recognized by T lymphocytes: At the core of cancer immunotherapy," Nature Reviews Cancer, 14:135-146 (Feb. 2014). Thirteen pages.
Dermer, G.B., "Another Anniversary for the War on Cancer," Bio/Technology 12, Mar. 1994, p. 320. Four pages.
Ezzell, C., "Cancer Vaccines: An Idea Whose Time Has Come?", The Journal of NIH Research 7, Jan. 1995, pp. 46-49. Four pages.
Freshney, I., "Culture of Animal Cells: A Manual of Basic Technique," Alan R. Liss, New York, p. 4 (1983). Four pages.
Gedde-Dahl III, T. et al. "T-cell Responses Against Products of Oncogenes: Generation and Characterization of Human T-cell Clones Specific for p21 Ras-Derived Synthetic Peptides," Human Immunology, 33:266-274 (Apr. 1992). Nine pages.
Gjertsen, M.K. et al., "Intradermal Ras Peptide Vaccination With Granulocyte-Macrophage Colony-Stimulating Factor As Adjuvant: Clinical and Immunological Responses in Patients With Pancreatic Adenocarcinoma," International Journal of Cancer, 92:441-450 (2001). Ten pages.
Gjertsen, M.K. et al., "Vaccination with mutant ras peptides and induction of T-cell responsiveness in pancreatic carcinoma patients carrying the corresponding RAS mutation," MPSRCH GENBANK, Abstract (Nov. 25, 1995). Two pages.
Golan, T. et al., "A phase I trial of a local delivery siRNA against k-ras in combination with chemotherapy for locally advanced pancreatic adenocarcinoma," Journal of Clinical Oncology, Abstract, 31(15) (May 20, 2013). One page.
Guo, C. et al., "Therapeutic Cancer Vaccines: Past, Present and Future," Adv Cancer Res. Author manuscript, Pub in final edited form: 119:421-475 (2013). Forty-five pages.
Gura, T., "Systems for Identifying New Drugs Are Often Faulty," Science, 278, Nov. 7, 1997, pp. 1041-1042. Two pages.
Haigh, P.I et al., "Vaccine Therapy for Patients with Melanoma," Oncology, Nov. 1999, pp. 1561-1582. Fifteen pages.
Hunger, R.E. et al., "Successful induction of immune responses against mutant ras in melanoma patients using intradermal injection of peptides and GM-CSF as adjuvant," Exp. Dermatology, 10:161-167 (2001). Seven pages.
International Preliminary Report on Patentability, dated Feb. 8, 2016, from International Application No. PCT/EP2014/077033, filed on Dec. 9, 2014. Nine pages.
International Preliminary Report on Patentability of the International Preliminary Examining Authority, dated Sep. 21, 2016, from International Application No. PCT/EP2015/059861, filed on May 5, 2015. Ten pages.
International Search Report and Written Opinion of the International Searching Authority, dated Jun. 18, 2015, from International Application No. PCT/EP2014/077033, filed on Dec. 9, 2014. Twenty-two pages.
International Search Report and Written Opinion of the International Searching Authority, dated Nov. 6, 2015, from International Application No. PCT/EP2015/059861, filed on May 5, 2015. Fifteen pages.
Jain, R.K., "Barriers to Drug Delivery in Solid Tumors," Scientific American 271(1): pp. 58-65. (1994). Eight pages.
Johansen, B.H. et al., "Binding of Ras Oncogene Peptides to Purified HLA-DQ($\alpha1*0102$, $\beta1*0602$) and -DR($\alpha$, $31*0101$) Molecules," Scandinavian Journal of Immunology, 39:607-612 (1994). Seven pages.
Johnson, R. et al., "The clinical impact of screening and other experimental tumor studies," Cancer Treatment Review (1975) pp. 1-31. Thirty-one pages.
Khleif, S.N. et al., "A phase I vaccine trial with peptides reflecting ras oncogene mutations of solid tumors," MPSRCH GENBANK, Abstract (Mar. 1999). Two pages.
Lurquin, C. (Boon, T.) et al., "Structure of the Gene of Tum-Transplantation Antigen P91A: The Mutated Exon Encodes a Peptide Recognized with Ld by Cytolytic T Cells," Cell, 58:293-303 (Jul. 28, 1989). Eleven pages.
Oettle, H. et al., "Adjuvant Chemotherapy With Gemcitabine vs Observation in Patients Undergoing Curative-Intent Resection of Pancreatic Cancer," JAMA, 297(3):267-277 (Jan. 17, 2007). Eleven pages.
Pardoll, D.M., "The blockade of immune checkpoints in cancer immunotherapy," Nature, 12:252-264 (Apr. 2012). Thirteen pages.
PCT Demand for International Preliminary Examination (Chapter II), filed on Mar. 7, 2016, from International Application No. PCT/EP2015/059861, filed on May 5, 2015. Nine pages.
PCT Response to Written Opinion of the International Preliminary Examining Authority, filed on Jun. 1, 2016, from International Application No. PCT/EP2015/059861, filed on May 5, 2015. Eleven pages.
PCT Response to Invitation, filed on Jun. 29, 2016, from International Application No. PCT/EP2015/059861, filed on May 5, 2015. Ten pages.
Pion, S. et al., "Shaping the Repertoire of Cytotoxic T-Lymphocyte Responses: Explanation for the Immunodominance Effect Whereby Cytotoxic T Lymphocytes Specific for Immunodominant Antigens Prevent Recognition of Nondominant Antigens," Blood, 93(3):952-962 (Feb. 1999). Twelve pages.
Prior, I.A. et al., "A comprehensive survey of Ras mutations in cancer," Cancer Research, 72(10):2457-2467 (May 15, 2012). Twenty pages.
Pubmed Ras protein Search Jan. 6, 2017. Seventeen pages.
Réjiba, S. et al., "K-ras oncogene silencing strategy reduces tumor growth and enhances gemcitabine chemotherapy efficacy for pancreatic cancer treatment," Cancer Science, 98(7):1128-1136 (Jul. 2007). Nine pages.
Spitler, L.E., "Cancer Vaccines: The Interferon Analogy," Cancer Biotherapy, 10(1), 1995. Three pages.
Strimpakos, A.S. et al., "Update on Phase I Studies in Advanced Pancreatic Adenocarcinoma. Hunting in Darkness?" Highlights from the "2013 ASCO Annual Meeting." Chicago, IL (May 30-Jun. 4, 2013); Journal of the Pancreas, 14(4):354-358 (Jul. 10, 2013). Five pages.
UniProtKB/Swiss-Prot accession No. P01112.1. Nineteen pages.
Weden, S., et al., "Long-term follow-up of pateints with resected pancreatic cancer following vaccination against mutant K-ras," International Journal of Cancer, 128:1120-1128 (2011). Nine pages.
Wijermans, P.W. et al., "Severe immunodeficiency in patients treated with fludarabine monophosphate," European Journal of Haematology, 50(5):292-296 (May 1993). Five pages.
Xue, W. et al., "Small RNA combination therapy for lung cancer," Proceedings of the National Academy of Sciences of the United States of America, 111(34):E3553-E3561 (Aug. 2014). Nine pages.
Black, C.A., "Delayed Type Hypersensitivity: Current Theories with an Historic Perspective," Dermatology Online Journal, 5(1):7 (1999). Ten pages.
Neoptolemos, J.P. et al., "Adjuvant Chemotherapy With Fluorouracil Plus Folinic Acid vs Gemcitabine Following Pancreatic Cancer

(56) References Cited

OTHER PUBLICATIONS

Resection: A Randomized Controlled Trial," JAMA, 304(10):1073-1081 (Sep. 8, 2010). Nine pages.
Nestle, F.O. et al., "Vaccination of melanoma patients with peptide- or tumor lysate-pulsed dendritic cells," Nature Medicine, 4(3):328-332 (Mar. 1998). Five pages.
Oettle, H. et al., "Adjuvant Chemotherapy With Gemcitabine and Long-term Outcomes Among Patients With Resected Pancreatic Cancer," JAMA, 310(14):1473-1481 (Oct. 9, 2013). Nine pages.
Sinn, M. et al., Perioperative treatment options in resectable pancreatic cancer—how to imporove long-term survival, World J. Gastrointenst Oncol, 8(3):248-257 (Mar. 15, 2016). Eleven pages.
Uesaka, K. et al., Adjuvant chemotherapy of S-1 versus gemcitabine for resected pancreatic cancer: a phase 3, open-label, randomised, non-inferiority trial (JASPAC 01), The Lancet, 388:248-257 (Jul. 16, 2016). Ten pages.
Van Laethem, J.L. et al., "Adjuvant Gemcitabine Alone Versus Gemcitabine-Based Chemoradiotherapy After Curative Resection for Pancreatic Cancer: A Randomized EORTC-40013-22012/FFCD-9203/GERCOR Phase II Study," J Clinical Oncol, 28(29):4450-4456 (Oct. 10, 2010). Seven pages.
Gouttefangeas, C., et al., "Differential Binding to Frequent HLA-A Alleles of p21 RAS Derived Peptides Bearing Oncogenic Substitutions at Position 12 or 13," Human Immunology, 55: 117-126 (1997).
Fossum, B., et al., "p21-ras-peptide-specific T-cell responses in a patient with colorectal cancer. CD4+ and CD8+ T-cells recognise a peptide corresponding to a common mutation (13Gly—Asp)", Int. J. Cancer, 56: 40-45 (1994).
Peace, D.J., et al., "Lysis of ras oncogene-transformed cells by specific cytotoxic T lymphocytes elicited by primary in vitro immunization with mutated ras peptide," J. Exp. Med., 179:473-479 (1994).
Ebner, C. et al., "Identification of Multiple T cell epitopes on Bet v I, the major birch pollen allergen, using specific T cell clones and overlapping peptides," Journal of Immunology, 150(3):1047-1054 (1993). Nine pages.
Royt et al., "Immunology", 2000, p. 159-163 (English translation of the relevant pages). 11 pages.
Royt et al., "Immunology", 2000, pp. 492-496 (English translation of the relevant pages). 11 pages.
Yarilin, A.A., "Principles of Immunology," 1999, pp. 221-223 and 228 (English translation of relevant pages). 6 pages.

\* cited by examiner

SEQUENCE LISTING

<160> NUMBER OF SEQ ID NOS: 33

<210> SEQ ID NO 1
<211> LENGTH: 30
<212> TYPE: PRT
<213> ORGANISM: Homo sapiens

<400> SEQUENCE: 1

Met Thr Glu Tyr Lys Leu Val Val Val Gly Ala Gly Cys Val Gly Lys
1               5                   10                  15

Ser Ala Leu Thr Ile Gln Leu Ile Gln Asn His Phe Val Asp
            20                  25                  30

<210> SEQ ID NO 2
<211> LENGTH: 30
<212> TYPE: PRT
<213> ORGANISM: Homo sapiens

<400> SEQUENCE: 2

Met Thr Glu Tyr Lys Leu Val Val Val Gly Ala Gly Arg Val Gly Lys
1               5                   10                  15

Ser Ala Leu Thr Ile Gln Leu Ile Gln Asn His Phe Val Asp
            20                  25                  30

<210> SEQ ID NO 3
<211> LENGTH: 30
<212> TYPE: PRT
<213> ORGANISM: Homo sapiens

<400> SEQUENCE: 3

Met Thr Glu Tyr Lys Leu Val Val Val Gly Ala Gly Asp Val Gly Lys
1               5                   10                  15

Ser Ala Leu Thr Ile Gln Leu Ile Gln Asn His Phe Val Asp
            20                  25                  30

<210> SEQ ID NO 4
<211> LENGTH: 30
<212> TYPE: PRT
<213> ORGANISM: Homo sapiens

<400> SEQUENCE: 4

Met Thr Glu Tyr Lys Leu Val Val Val Gly Ala Gly Val Val Gly Lys
1               5                   10                  15

Ser Ala Leu Thr Ile Gln Leu Ile Gln Asn His Phe Val Asp
            20                  25                  30

<210> SEQ ID NO 5
<211> LENGTH: 30
<212> TYPE: PRT
<213> ORGANISM: Homo sapiens

<400> SEQUENCE: 5

Met Thr Glu Tyr Lys Leu Val Val Val Gly Ala Gly Ala Val Gly Lys
1               5                   10                  15

Ser Ala Leu Thr Ile Gln Leu Ile Gln Asn His Phe Val Asp
            20                  25                  30

<210> SEQ ID NO 6
<211> LENGTH: 30
<212> TYPE: PRT
<213> ORGANISM: Homo sapiens

<400> SEQUENCE: 6

-continued

Met Thr Glu Tyr Lys Leu Val Val Val Gly Ala Gly Ser Val Gly Lys
1               5                   10                  15

Ser Ala Leu Thr Ile Gln Leu Ile Gln Asn His Phe Val Asp
            20                  25                  30

<210> SEQ ID NO 7
<211> LENGTH: 30
<212> TYPE: PRT
<213> ORGANISM: Homo sapiens

<400> SEQUENCE: 7

Met Thr Glu Tyr Lys Leu Val Val Val Gly Ala Ala Gly Val Gly Lys
1               5                   10                  15

Ser Ala Leu Thr Ile Gln Leu Ile Gln Asn His Phe Val Asp
            20                  25                  30

<210> SEQ ID NO 8
<211> LENGTH: 29
<212> TYPE: PRT
<213> ORGANISM: Homo sapiens

<400> SEQUENCE: 8

Met Thr Glu Tyr Lys Leu Val Val Val Gly Ala Cys Gly Val Gly Lys
1               5                   10                  15

Ser Ala Leu Thr Ile Gln Leu Ile Gln Asn His Phe Val
            20                  25

<210> SEQ ID NO 9
<211> LENGTH: 30
<212> TYPE: PRT
<213> ORGANISM: Homo sapiens

<400> SEQUENCE: 9

Met Thr Glu Tyr Lys Leu Val Val Val Gly Ala Asp Gly Val Gly Lys
1               5                   10                  15

Ser Ala Leu Thr Ile Gln Leu Ile Gln Asn His Phe Val Asp
            20                  25                  30

<210> SEQ ID NO 10
<211> LENGTH: 30
<212> TYPE: PRT
<213> ORGANISM: Homo sapiens

<400> SEQUENCE: 10

Met Thr Glu Tyr Lys Leu Val Val Val Gly Ala Arg Gly Val Gly Lys
1               5                   10                  15

Ser Ala Leu Thr Ile Gln Leu Ile Gln Asn His Phe Val Asp
            20                  25                  30

<210> SEQ ID NO 11
<211> LENGTH: 30
<212> TYPE: PRT
<213> ORGANISM: Homo sapiens

<400> SEQUENCE: 11

Met Thr Glu Tyr Lys Leu Val Val Val Gly Ala Ser Gly Val Gly Lys
1               5                   10                  15

Ser Ala Leu Thr Ile Gln Leu Ile Gln Asn His Phe Val Asp
            20                  25                  30

<210> SEQ ID NO 12

```
<211> LENGTH: 30
<212> TYPE: PRT
<213> ORGANISM: Homo sapiens

<400> SEQUENCE: 12

Met Thr Glu Tyr Lys Leu Val Val Gly Ala Val Gly Val Gly Lys
1               5                   10                  15

Ser Ala Leu Thr Ile Gln Leu Ile Gln Asn His Phe Val Asp
                20                  25                  30

<210> SEQ ID NO 13
<211> LENGTH: 30
<212> TYPE: PRT
<213> ORGANISM: Homo sapiens

<400> SEQUENCE: 13

Asp Gly Glu Thr Cys Leu Leu Asp Ile Leu Asp Thr Ala Gly Arg Glu
1               5                   10                  15

Glu Tyr Ser Ala Met Arg Asp Gln Tyr Met Arg Thr Gly Glu
                20                  25                  30

<210> SEQ ID NO 14
<211> LENGTH: 30
<212> TYPE: PRT
<213> ORGANISM: Homo sapiens

<400> SEQUENCE: 14

Asp Gly Glu Thr Cys Leu Leu Asp Ile Leu Asp Thr Ala Gly Lys Glu
1               5                   10                  15

Glu Tyr Ser Ala Met Arg Asp Gln Tyr Met Arg Thr Gly Glu
                20                  25                  30

<210> SEQ ID NO 15
<211> LENGTH: 30
<212> TYPE: PRT
<213> ORGANISM: Homo sapiens

<400> SEQUENCE: 15

Asp Gly Glu Thr Cys Leu Leu Asp Ile Leu Asp Thr Ala Gly His Glu
1               5                   10                  15

Glu Tyr Ser Ala Met Arg Asp Gln Tyr Met Arg Thr Gly Glu
                20                  25                  30

<210> SEQ ID NO 16
<211> LENGTH: 30
<212> TYPE: PRT
<213> ORGANISM: Homo sapiens

<400> SEQUENCE: 16

Asp Gly Glu Thr Cys Leu Leu Asp Ile Leu Asp Thr Ala Gly Leu Glu
1               5                   10                  15

Glu Tyr Ser Ala Met Arg Asp Gln Tyr Met Arg Thr Gly Glu
                20                  25                  30

<210> SEQ ID NO 17
<211> LENGTH: 30
<212> TYPE: PRT
<213> ORGANISM: Homo sapiens

<400> SEQUENCE: 17

Asp Gly Glu Thr Cys Leu Leu Asp Ile Leu Asp Thr Ala Gly Glu Glu
1               5                   10                  15
```

Glu Tyr Ser Ala Met Arg Asp Gln Tyr Met Arg Thr Gly Glu
            20                  25                  30

<210> SEQ ID NO 18
<211> LENGTH: 30
<212> TYPE: PRT
<213> ORGANISM: Homo sapiens

<400> SEQUENCE: 18

Asp Gly Glu Thr Cys Leu Leu Asp Ile Leu Asp Thr Ala Gly Pro Glu
1               5                   10                  15

Glu Tyr Ser Ala Met Arg Asp Gln Tyr Met Arg Thr Gly Glu
            20                  25                  30

<210> SEQ ID NO 19
<211> LENGTH: 17
<212> TYPE: PRT
<213> ORGANISM: Homo sapiens

<400> SEQUENCE: 19

Lys Leu Val Val Val Gly Ala Gly Cys Val Gly Lys Ser Ala Leu Thr
1               5                   10                  15

Ile

<210> SEQ ID NO 20
<211> LENGTH: 17
<212> TYPE: PRT
<213> ORGANISM: Homo sapiens

<400> SEQUENCE: 20

Lys Leu Val Val Val Gly Ala Gly Asp Val Gly Lys Ser Ala Leu Thr
1               5                   10                  15

Ile

<210> SEQ ID NO 21
<211> LENGTH: 17
<212> TYPE: PRT
<213> ORGANISM: Homo sapiens

<400> SEQUENCE: 21

Lys Leu Val Val Val Gly Ala Ala Gly Val Gly Lys Ser Ala Leu Thr
1               5                   10                  15

Ile

<210> SEQ ID NO 22
<211> LENGTH: 17
<212> TYPE: PRT
<213> ORGANISM: Homo sapiens

<400> SEQUENCE: 22

Lys Leu Val Val Val Gly Ala Cys Gly Val Gly Lys Ser Ala Leu Thr
1               5                   10                  15

Ile

<210> SEQ ID NO 23
<211> LENGTH: 17
<212> TYPE: PRT
<213> ORGANISM: Homo sapiens

<400> SEQUENCE: 23

Lys Leu Val Val Val Gly Ala Asp Gly Val Gly Lys Ser Ala Leu Thr
1               5                   10                  15

Ile

<210> SEQ ID NO 24
<211> LENGTH: 17
<212> TYPE: PRT
<213> ORGANISM: Homo sapiens

<400> SEQUENCE: 24

Lys Leu Val Val Val Gly Ala Arg Gly Val Gly Lys Ser Ala Leu Thr
1               5                   10                  15

Ile

<210> SEQ ID NO 25
<211> LENGTH: 17
<212> TYPE: PRT
<213> ORGANISM: Homo sapiens

<400> SEQUENCE: 25

Lys Leu Val Val Val Gly Ala Ser Gly Val Gly Lys Ser Ala Leu Thr
1               5                   10                  15

Ile

<210> SEQ ID NO 26
<211> LENGTH: 17
<212> TYPE: PRT
<213> ORGANISM: Homo sapiens

<400> SEQUENCE: 26

Lys Leu Val Val Val Gly Ala Val Gly Val Gly Lys Ser Ala Leu Thr
1               5                   10                  15

Ile

<210> SEQ ID NO 27
<211> LENGTH: 17
<212> TYPE: PRT
<213> ORGANISM: Homo sapiens

<400> SEQUENCE: 27

Lys Leu Val Val Val Gly Ala Gly Arg Val Gly Lys Ser Ala Leu Thr
1               5                   10                  15

Ile

<210> SEQ ID NO 28
<211> LENGTH: 17
<212> TYPE: PRT
<213> ORGANISM: Homo sapiens

<400> SEQUENCE: 28

Lys Leu Val Val Val Gly Ala Gly Val Val Gly Lys Ser Ala Leu Thr
1               5                   10                  15

Ile

<210> SEQ ID NO 29
<211> LENGTH: 17
<212> TYPE: PRT
<213> ORGANISM: Homo sapiens

<400> SEQUENCE: 29

Leu Asp Ile Leu Asp Thr Ala Gly Arg Glu Glu Tyr Ser Ala Met Arg
1               5                   10                  15

Asp

<210> SEQ ID NO 30
<211> LENGTH: 17
<212> TYPE: PRT
<213> ORGANISM: Homo sapiens

<400> SEQUENCE: 30

Leu Asp Ile Leu Asp Thr Ala Gly Lys Glu Glu Tyr Ser Ala Met Arg
1               5                   10                  15

Asp

<210> SEQ ID NO 31
<211> LENGTH: 17
<212> TYPE: PRT
<213> ORGANISM: Homo sapiens

<400> SEQUENCE: 31

Leu Asp Ile Leu Asp Thr Ala Gly His Glu Glu Tyr Ser Ala Met Arg
1               5                   10                  15

Asp

<210> SEQ ID NO 32
<211> LENGTH: 17
<212> TYPE: PRT
<213> ORGANISM: Homo sapiens

<400> SEQUENCE: 32

Leu Asp Ile Leu Asp Thr Ala Gly Leu Glu Glu Tyr Ser Ala Met Arg
1               5                   10                  15

Asp

<210> SEQ ID NO 33
<211> LENGTH: 189
<212> TYPE: PRT
<213> ORGANISM: Homo sapiens

<400> SEQUENCE: 33

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Val Pro Met Val
                100                 105                 110

Leu Val Gly Asn Lys Cys Asp Leu Ala Ala Arg Thr Val Glu Ser Arg
            115                 120                 125

Gln Ala Gln Asp Leu Ala Arg Ser Tyr Gly Ile Pro Tyr Ile Glu Thr
        130                 135                 140

Ser Ala Lys Thr Arg Gln Gly Val Glu Asp Ala Phe Tyr Thr Leu Val
145                 150                 155                 160

-continued

```
Arg Glu Ile Arg Gln His Lys Leu Arg Lys Leu Asn Pro Pro Asp Glu
                165                 170                 175
Ser Gly Pro Gly Cys Met Ser Cys Lys Cys Val Leu Ser
                180                 185
```

PEPTIDE MIXTURE

RELATED APPLICATIONS

This application is a Division of U.S. application Ser. No. 15/102,681, filed on Jun. 8, 2016, which is a § 371 National Phase Application of International Application No. PCT/EP2014/077033, filed on Dec. 9, 2014, which claims priority to European Application No. 13196333.2, filed on Dec. 9, 2013, all of which are incorporated herein by reference in their entirety.

FIELD OF THE INVENTION

The present invention provides peptide mixtures comprising peptides of the RAS protein for eliciting an immune response, peptides of the RAS protein for eliciting an immune response, and T-cell mixtures and T-cell preparations comprising T-cells specific for such peptides when presented on MHC molecules. The invention also relates to pharmaceutical formulations comprising such peptide mixtures and T-cell mixtures and preparations, uses of such peptide mixtures, peptides and T-cell mixtures and preparations for the prophylaxis and/or treatment of cancer, and methods of selecting peptide mixtures, peptides, T-cell mixtures and T-cell preparations for the treatment of cancer.

BACKGROUND OF THE INVENTION

The genetic background for the onset of cancer is alterations in proto-oncogenes, oncogenes and tumour suppressor genes. Proto-oncogenes are normal genes of the cell which have the potential of becoming oncogenes. All oncogenes code for and function through a protein. In the majority of cases they have been shown to be components of signal transduction pathways. Oncogenes arise in nature from proto-oncogenes through point mutations or translocations, thereby resulting in a transformed state of the cell harbouring the mutation. Cancer develops through a multi-step process involving several mutational events in oncogenes and tumour suppressor cells.

In its simplest form, a single base substitution in a proto-oncogene may cause the encoded protein to differ in one amino acid.

In experimental models involving murine tumours, it has been shown that point mutations in intracellular "self"-proteins may give rise to tumour rejection antigens consisting of peptides differing in a single amino acid from the normal peptide. The T cells recognizing these peptides in the context of major histocompatibility (MHC) molecules on the surface of the tumour cells are capable of killing the tumour cells and thus rejecting the tumour from the host. (Boon, T. et al, Cell 1989, Vol. 58, p. 293-303)

In the last three decades, particular effort has been devoted to the analysis of antibodies to human tumour antigens. It has been suggested that such antibodies could be used both for diagnostic and therapeutic purposes, for instance in connection with an anti-cancer agent. One problem is that antibodies can only bind to tumour antigens that are exposed on the surface of tumour cells. For this reason the efforts to produce a cancer treatment based on the immune system of the body has been less successful than expected.

Antibodies typically recognise free antigens in native conformation and can potentially recognise almost any site exposed on the antigen surface. In contrast to the antibodies produced by the B cells, T cells recognise antigens only in the context of MHC molecules, designated HLA (human leukocyte antigen) in humans, and only after appropriate antigen processing, usually consisting of proteolytic fragmentation of the protein, resulting in peptides that fit into the groove of the MHC molecules. This enables cells to recognise peptides derived from intracellular proteins. T cells can thus recognise aberrant peptides derived from anywhere in the tumour cell, when displayed on the surface of the tumour cell by MHC molecules. The T cell can subsequently be activated to eliminate the tumour cell harbouring the aberrant peptide.

T cells may control the development and growth of cancer by a variety of mechanisms. Cytotoxic T cells, both HLA class I restricted CD8+ and HLA Class II restricted CD4+, may directly kill tumour cells carrying the appropriate tumour antigens. CD4+ helper T cells are needed for induction and maintenance of cytotoxic T cell responses as well as for antibody responses, and for inducing macrophage and lymphokine-activated killer cell (LAK cell) killing.

Many oncogenes and their protein products have been identified. In addition, it has been shown that the cell repertoire of a healthy person includes T cells with specificity against a synthetic peptide fragment derived from one p21 RAS oncogene product, when presented on an appropriate HLA molecule. Furthermore, it is anticipated that approximately 20% of all cancers are associated with a mutation in the RAS oncogene.

There are great concerns about using peptide mixtures for vaccination of patients due to the risk that some of the peptides in the mixture are immunodominant and thus suppress the HLA presentation of the other peptides (Pion S, et al., Blood, 1999 Feb. 1; 93(3): p952-62). From experiments performed in vitro, it is known that various mutated RAS peptides may compete for binding to the HLA molecule responsible for presentation to the relevant T cells and that peptides of the same length, but representing different mutations may inhibit the binding and recognition of a peptide representing another mutation with different degrees of efficacy (T. Gedde-Dahl III et al., Human Immunol. 1994, 33, p. 266-274, and B. H. Johanssen et al., Scand. J. Immunol., 1994, 33, p. 607-612). From these facts, the immunodominance issue has been regarded as a problem for mutated RAS peptide vaccines.

WO 92/14756 discloses synthetic peptides and fragments of oncogene protein products which elicit T cell immunity, for use in vaccines against cancers associated with RAS and compositions for the treatment of cancer. The peptides must correspond to an active fragment of the oncogene as presented by the cancer cell and include a mutation in one or more positions corresponding to the oncogene mutation. This document discloses mutations at positions 12, 13 and 61 of the RAS protein and specifically discloses only G12A, G12V, G12C, G12S, G12K, G12D, G12R, Q61R, Q61K, Q61L, Q61H, G13V and G13D mutations. In addition, while this document mentions that vaccines may comprise a selection of peptides having the most common mutations found in oncogene proteins, it does not suggest any specific combinations.

WO 00/66153 discusses synthetic peptide mixtures which elicit T cell immunity for use in cancer vaccines. The peptide mixtures consist of RAS p21 mutant peptides and this document specifically discloses only G12A, G12C, G12D, G12R, G12S, G12V, Q61H, Q61K, Q61L, Q61R and G13D mutations. This document also discloses that the immune response elicited by a cocktail of peptides was significantly higher than that elicited by a single peptide; however, it does not suggest that any other combinations of peptides other than those specifically disclosed therein may be useful.

GB 2328689 discloses that a peptide capable of inducing specific cytotoxic T cell responses (CD 8+) comprises 8 to 10 amino acids of the p21 ras proto-oncogene protein including position comprise position 12 and/or 13, or position 61, of the p21 RAS proto-oncogene protein and have an amino acid substitution in position 12, 13 or 61. This document also discloses that the peptide may be used as a cancer vaccine and in compositions for anti-cancer treatment. However, no specific peptide mixtures are disclosed as being particularly useful.

Furthermore, neither of these documents discusses how particular peptides are associated with particular types of cancer, and do not address the redundancy of peptides in mixtures comprising a number of peptides.

Gjertsen et al. (Int, J. Cancer 2001, 92, p. 441-450) discloses a phase I/II trial involving patients with adenocarcinoma of the pancreas vaccinated with synthetic mutant RAS peptides in combination with granulocyte-macrophage colony-stimulating factor. This trial used single peptide vaccines or a mixture of four mutant peptides. The combination vaccine consisted of the four most common K-RAS mutations found in pancreatic adenocarcinoma, namely peptides having a G12V, a G12D, a G12C or a G12R mutation. However, this document does not disclose any other combinations of peptides that may be useful, does not disclose any other mutations of the RAS protein that are associated with cancer, and does not discuss how particular peptides are associated with particular types of cancer.

Wedén et al. (Int. J. Cancer 2010, 128(5), p. 1120-1128) reports the long-term follow-up of patients with pancreatic adenocarcinoma vaccinated with synthetic mutant RAS peptides. The vaccine consisted of either a single RAS peptide or a cocktail of seven RAS peptides. In particular, the seven RAS peptides used in this trial had a G12A, a G12C, a G12D, a G12R, a G12S, a G12V or a G13D mutation. However, this document does not discuss how particular peptides are associated with particular types of cancer, and does not disclose any other combinations of peptides which may be useful.

Hunger et al. (Exp. Dermatol. 2001, 10: 161-167) reports a clinical pilot study of the in vivo immunogenicity of RAS peptides with safety as the primary end point and immunogenicity of RAS peptides as a secondary end point. Melanoma patients were immunised intradermally with N-ras peptides 9 residue 49-73) with four codon 61 mutations. Eight of the patients showed positive responses. However, this document does not discuss how particular peptides are associated with particular types of cancer, and does not disclose any other combinations of peptides which may be useful.

Prior et al. (Cancer Res. 2012, 72(10), p. 2457-2467) discloses that different types of cancer are coupled to mutation of a particular RAS isoform and that each isoform has a distinctive codon mutation signature. In addition, Prior et al. discloses that a total of 18 mutations occur in positions 12, 13 and 61 of the RAS protein, with six mutations occurring in each position. This review also discusses the effects of these mutations on RAS function and the potential mechanisms leading to differential patterns of RAS isoform mutations. However, this document does not address the treatment or prophylaxis of cancer, or the issue of immunodominance and redundancy within a vaccine. In addition, there is no disclosure of a vaccine or treatment against cancer, and this document does not disclose any combinations of peptides which may be useful.

Thus, there is a need to provide further and more effective cancer vaccines and/or treatments. In particular there is a need to provide vaccines and/or treatments which are targeted to particular cancers, which overcome issues of immunodominance and redundancy, and which are cost-effective.

SUMMARY OF INVENTION

The present invention provides solutions to the problems discussed above because it has now been found that peptide mixtures comprising at least two peptides having point mutations at the amino acid corresponding to position 13 of the RAS protein, wherein each peptide has a different mutation, can be used as a vaccine against and/or a treatment for cancers associated with a RAS protein mutation. In particular, it has been found that at least some of the peptide mixtures of the present invention can be used as vaccines against and/or treatments for over 99% of cancers associated with mutations in RAS proteins. The peptide mixtures of the present invention alleviate issues of immunodominance and reduce the redundancy of active ingredients within a pharmaceutical composition, thus making the peptide mixtures more cost-effective vaccines and/or treatments. In addition, the present invention allows for vaccination and/or treatment that is targeted to specific types of cancer and methods of selecting mixtures of peptides targeted to specific types of cancer.

Thus, in a first aspect of the invention, there is provided a peptide mixture suitable for eliciting an immune response comprising a first and a second peptide, each corresponding to a fragment of the RAS protein wherein each of the first and second peptides comprises a region of at east 8 amino acids which includes position 13 of the RAS protein, each of said regions of the first and second peptides independently has at least 6 amino acid residues, other than at said position 13, which are identical to the corresponding region of the RAS protein, each of the first and the second peptides has a point mutation at the amino acid corresponding to said position 13, and the point mutation of the first peptide is different from the point mutation of the second peptide.

Advantageously, each of the point mutations is independently selected from a G13A, G13C, G13D, G13R, G13S or a G13V mutation.

Preferably, the peptide mixture further comprises at least one further peptide corresponding to a fragment of the RAS protein comprising a region of a least 8 amino acids which includes position 12 of the RAS protein, wherein each of said regions of the at least one further peptides independently has at least 6 amino acid residues other than at said position 12, which are identical to the corresponding region of the RAS protein, and wherein there is a point mutation at the amino acid corresponding to position 12 of the RAS protein; and/or at least one further peptide corresponding to a fragment of the RAS protein comprising a region of a least 8 amino acids which includes position 61 of the RAS protein, wherein each of said regions of the at least one further peptides independently has at least 6 amino acid residues other than at said position 61, which are identical to the corresponding region of the RAS protein, and wherein there is a point mutation at the amino acid corresponding to position 61 of the RAS protein.

Conveniently, the point mutation at the amino acid corresponding to position 12 of the RAS protein is selected from a G12A, G12C, G12D, G12R, G12S or a G12V mutation and/or the point mutation at the amino acid corresponding to position 61 of the RAS protein is selected from a Q61E, Q61H, Q61K, Q61L, a Q61P or a Q61R mutation.

Advantageously, the point mutation of the first or second peptide is a G13C mutation.

Conveniently, the point mutation of the first or second peptide is a G13R mutation.

Preferably, the point mutation of the first or second peptide is a G13D mutation.

Conveniently, the point mutation of the first or second peptide is a G13V mutation.

Advantageously, the point mutation of the first and/or second peptide is selected from a G13C, a G13D, a G13R and a G13V mutation.

Preferably, the first peptide is a peptide having a G13C mutation and the second peptide is a peptide having a G13D mutation, and the at least one further peptide comprises:
  a peptide having a G12A mutation,
  a peptide having a G12C mutation,
  a peptide having a G12D mutation,
  a peptide having a G12R mutation,
  a peptide having a G12S mutation, and
  a peptide having a G12V mutation Advantageously, the first peptide is a peptide having a G13R mutation and the second peptide is a peptide having a G13V mutation, and the at least one further peptide comprises:
  a peptide having a Q61H mutation,
  a peptide having a Q61K mutation,
  a peptide having a Q61L mutation, and
  a peptide having a Q61R mutation.

Conveniently, the peptide mixture comprises at least a third peptide.

Preferably, the third peptide is a peptide corresponding to a fragment of the RAS protein comprising a region of a least 8 amino acids which includes position 13 of the RAS protein, said region of the third peptide has at least 6 amino acid residues other than at position 13, which are identical to the corresponding region of the RAS protein, and there is a point mutation at the amino acid corresponding to position 13 of the RAS protein which is different from the point mutations of the first and second peptides.

Conveniently, the point mutation of the third peptide is selected from a G13C, a G13D, a G13R and a G13V mutation.

Advantageously, the peptide mixture comprises a maximum of 8 different peptides.

Conveniently, the peptide mixture further consists of a third and fourth peptide, each corresponding to a fragment of the RAS protein wherein:
  each of the third and fourth peptides comprises a region of at least 8 amino acids which includes position 13 of the RAS protein,
  each of said regions of the third and fourth peptides independently has at least 6 amino acid residues other than at said position 13, which are identical to the corresponding region of the RAS protein,
  each of the third and fourth peptides has a point mutation at the amino acid corresponding to said position 13, and
  the point mutation of each of the peptides is different from the point mutation of the other peptides, wherein
  the first peptide is a peptide having a G13R mutation,
  the second peptide is a peptide having a G13A mutation,
  the third peptide is a peptide having a G13S mutation, and
  the fourth peptide is a peptide having a G13V mutation.

In second aspect of the invention, there is provided a peptide mixture suitable for eliciting an immune response comprising at least five peptides, each corresponding to a fragment of the RAS protein wherein:
  each of the at least five peptides comprises a region of at least 8 amino acids and includes position 13 of the RAS protein,
  each of said regions of the at least five peptides independently has at least 6 amino acid residues other than at said position 13, which are identical to the corresponding region of the RAS protein,
  each of the peptides has a point mutation at the amino acid corresponding to said position 13, selected from a G13A, G13C, G13D, G13R, G13S or a G13V mutation, and
  the point mutation of each peptide is different from the point mutation of the other peptides.

In a third aspect of the invention, there is provided a peptide mixture suitable for eliciting an immune response consisting of six peptides each corresponding to a fragment of the RAS protein wherein:
  each peptide comprises a region of at least 8 amino acids which includes position 12 of the RAS protein,
  each of said regions of the peptides independently has at least 6 amino acid residues other than at said position 12, which are identical to the corresponding region of the RAS protein,
  each of the peptides has a point mutation at the amino acid corresponding to said position 12, selected from a G12A, G12C, G12D, G12R, G12S or a G12V mutation, and
  the point mutation of each peptide is different from the point mutation of the other peptides.

In fourth aspect of the invention, there is provided a peptide mixture suitable for eliciting an immune response consisting of six peptides each corresponding to a fragment of the RAS protein wherein:
  each peptide comprises a region of at least 8 amino acids which includes position 61 of the RAS protein,
  each of said regions of the peptides independently has at least 6 amino acid residues other than at said position 61, which are identical to the corresponding region of the RAS protein,
  each of the peptides has a point mutation at the amino acid corresponding to said position 61, selected from a Q61E, Q61H, Q61K, Q61L, a Q61P or a Q61R mutation, and
  the point mutation of each peptide is different from the point mutation of the other peptides.

In a fifth aspect of the invention, there is provided a peptide mixture suitable for eliciting an immune response consisting of a first, second, third and fourth peptide each corresponding to a fragment of the RAS protein wherein each of the first, second and third peptides comprises a region of at least 8 amino acids which includes position 12 of the RAS protein, the fourth peptide comprises a region of at least 8 amino acids which includes position 13 of the RAS protein, each of said regions of the first, second, third and fourth peptides independently has at least 6 amino acid residues other than at said position 12 or 13 respectively, which are identical to the corresponding region of the RAS protein, each of the first, second, third and fourth peptides has a point mutation at the amino acid corresponding to said position 12 or 13 respectively, and
  the first peptide is a peptide having a G12A mutation,
  the second peptide is a peptide having a G12R mutation,
  the third peptide is a peptide having a G12S mutation, and
  the fourth peptide is a peptide having a G13C mutation.

Advantageously, in all aspects of the invention, each peptide, outside of said region including positions 12, 13 or 61, has at least 75% sequence identity to the RAS protein.

In a sixth aspect of the invention, there is provided, a peptide for use as a vaccine or medicament and which corresponds to a fragment of the RAS protein wherein:

the peptide comprises a region of at least 8 amino acids which includes position 13 of the RAS protein, said region has at least 6 amino acid residues, other than at said position 13, which are identical to the corresponding region of the RAS protein, and the peptide has a G13C, or a G13R point mutation at the amino acid corresponding to said position 13, In a seventh aspect of the invention, there is provided a peptide suitable for eliciting an immune response and which corresponds to a fragment of the RAS protein wherein:

the peptide comprises a region of at least 8 amino acids which includes position 13 of the RAS protein, said region has at least 6 amino acid residues, other than at said position 13, which are identical to the corresponding region of the RAS protein, and the peptide has a G13C or a G13R point mutation at the amino acid corresponding to said position 13.

In an eighth aspect of the invention, there is provided a peptide suitable for eliciting an immune response and which corresponds to a fragment of the RAS protein wherein:

the peptide comprises a region of at least 8 amino acids which includes position 13 of the RAS protein, said region has at least 6 amino acid residues, other than at said position 13, which are identical to the corresponding region of the RAS protein, the peptide comprises no more than 30 amino acid residues, and the peptide has a G13C or a G13R point mutation at the amino acid corresponding to said position 13.

In a ninth aspect of the invention, there is provided a T-cell mixture comprising T-cells specific for each of the peptides in one of the peptide mixtures according to any one of the first to fifth aspects described above or a T-cell preparation comprising T-cells specific for one of the peptides for use according to the sixth aspect or a peptide according to the seventh or eighth aspect of the invention described above, when presented on an MHC molecule.

In a tenth aspect of the invention, there is provided a pharmaceutical composition comprising the peptide mixture of any of the first to fifth aspects described above, a peptide for use according to the sixth aspect described above, a peptide according to the seventh or eighth aspect described above or the T-cell mixture or T-cell preparation according to the ninth aspect described above and a pharmaceutically acceptable carrier, diluent and/or excipient.

Preferably, the peptide mixture, peptide, peptide for use, T-cell mixture, T-cell preparation or pharmaceutical composition of any of the aspects described above is for use in the prophylaxis and/or treatment of cancer.

Conveniently, the cancer is adrenal gland, autonomic ganglia, biliary tract, bone, breast, central nervous system, cervical, colorectal, endometrial, haematopoietic, lymphoid, kidney, large intestine, liver, lung, oesophagus, ovarian, pancreatic, prostate, salivary gland, skin, small intestine, stomach, testicular, thymus, thyroid, upper aerodigestive tract and urinary tract cancer and/or malignant melanoma.

Advantageously, the cancer is colorectal, lung and/or pancreatic cancer.

Conveniently. the peptide mixture, peptide, peptide for use, T-cell mixture, T-cell preparation or pharmaceutical composition according to the aspects described above is for use in the prophylaxis and/or treatment of malignant melanoma.

In an eleventh aspect of the invention, there is provided a method of treating or preventing cancer comprising administering a peptide mixture according to any one of the first to fifth aspects, a peptide for use according to the sixth aspect, a peptide according to the seventh or eighth aspect, a T-cell mixture or T-cell preparation according to the ninth aspect or a pharmaceutical composition according to the tenth aspect described above.

In a twelfth aspect of the invention, there is provided a peptide mixture, a peptide for use as a vaccine or medicament, a peptide, a T-cell mixture, a T-cell preparation or a pharmaceutical composition for use in a method comprising:

i) identifying RAS protein mutations present in a sample taken from a patient;

ii) selecting a peptide mixture according to any one of the first to fifth aspects described above comprising a peptide comprising a point mutation corresponding to at least one of the RAS protein mutations identified in the sample; or selecting a peptide for use according to the sixth aspect described above comprising a point mutation corresponding to at least one of the RAS protein mutations identified in the sample; or selecting a peptide according to the seventh or eighth aspect described above comprising a point mutation corresponding to at least one of the RAS protein mutations identified in the sample; or selecting a T-cell mixture or T-cell preparation according to the ninth aspect described above, comprising T-cells specific for a peptide, when presented on an MHC molecule, comprising a point mutation corresponding to at least one of the RAS protein mutations identified in the sample; or selecting a pharmaceutical composition according to the tenth aspect described above comprising a peptide mixture, peptide for use as a vaccine or medicament or a peptide comprising a point mutation corresponding to at least one of the RAS protein mutations identified in the sample, or a T-cell mixture or T-cell preparation comprising T-cells specific for a peptide, when presented on an MHC molecule, comprising a point mutation corresponding to at least one of the RAS protein mutations identified in the sample and iii) administering the peptide mixture, peptide for use, peptide, T-cell mixture of T-cell preparation to the patient.

In a thirteenth aspect of the invention, there is provided a method of selecting a peptide mixture, a peptide for use as a vaccine or medicament, a peptide, a T-cell mixture, a. T-cell preparation or a pharmaceutical composition for administration to a patient comprising:

i) identifying RAS protein mutations present in a sample taken from a patient; and ii) selecting a peptide mixture according to any one of the first to fifth aspects described above comprising a peptide comprising a point mutation corresponding to at least one of the RAS protein mutations identified in the sample; or selecting a peptide for use according to the sixth aspect described above; or selecting a peptide according to the seventh or eighth aspect described above; or selecting a T-cell mixture or T-cell preparation according to the ninth aspect described above comprising T-cells specific for a peptide, when presented on an MHC molecule, comprising a point mutation corresponding to at least one of the RAS protein mutations identified in the sample; or selecting a pharmaceutical composition according to the tenth aspect described above comprising a peptide mixture, peptide for use as a vaccine or medicament or a peptide comprising a point mutation corresponding to at least one of the RAS protein mutations identified in the sample, or a T-cell mixture or T-cell preparation comprising T-cells specific for a peptide, when presented on an MHC molecule, comprising a point mutation corresponding to at least one of the RAS protein mutations identified in the sample.

In fourteenth aspect of the invention, there is provided use of a peptide mixture according to any one of the first to fifth aspects described above, a peptide for use according to the sixth aspect described above or a peptide according to the seventh or eighth aspect described above for the preparation of a T-cell mixture or T-cell preparation according to the ninth aspect described above.

The peptide mixtures, peptides for use and peptides described above are generally isolated from their natural environment.

The term "peptide" as used herein, refers to a polymer of amino acid residues that is (or has a sequence that corresponds to) a fragment of a longer protein. The term also applies to amino acid polymers in which one or more amino acid residues is a modified residue, or a non-naturally occurring residue, such as an artificial chemical mimetic of a corresponding naturally-occurring amino acid, as well as to naturally occurring amino acid polymers.

The percentage "identity" between two sequences may be determined using the BLASTP algorithm version 2.2.2 (Altschul, Stephen F., Thomas L Madden, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402) using default parameters. In particular, the BLAST algorithm can be accessed on the internet at ncbi.nlm.nih.gov/blast/.

The term "immune response", as used herein, refers in some embodiments to a T cell-mediated immune response upon presentation of a peptide by major histocompatibility (MHC) molecules on the surface of cells, and in particular refers to activation of T cells upon presentation of peptide.

The term "RAS protein", as used herein, refers to the class of small GTPase proteins encoded by the ras proto-oncogene and includes all three isoforms of the RAS protein: HRAS, KRAS and NRAS. In some embodiments, the term "RAS protein" refers to the protein corresponding to UniProtKB/Swiss-Prot accession number P01112.1 and as shown in SEQ ID NO:33.

The term "position 13 of the RAS protein", as used herein, refers to the thirteenth amino acid in the amino acid chain forming the primary structure of the wild-type RAS protein, counting from the N-terminal.

The term "position 12 of the RAS protein", as used herein, refers to the twelfth amino acid in the amino acid chain forming the primary structure of the wild-type RAS protein, counting from the N-terminal.

The term "position 61 of the RAS protein", as used herein, refers to the sixty-first amino acid in the amino acid chain forming the primary structure of the wild-type RAS protein, counting from the N-terminal.

The term "the amino acid corresponding to position 13", as used herein, means an amino acid in a peptide of a RAS protein located in the peptide's amino acid chain at a position corresponding to the thirteenth amino acid of the amino acid sequence of the RAS protein, counting from the N-terminal. Corresponding meanings are attributed to the terms "the amino acid corresponding to position 12" and "the amino acid corresponding to position 61".

The term "peptide mixture", as used herein, refers to two or more peptides which are mixed but not chemically combined. The mixtures may be present as a dry powder, solution, suspension or colloid, and may be homogeneous or heterogeneous.

The term "RAS protein mutations", as used herein, refers to one or more point mutations present in the RAS proteins present in a sample taken from a subject.

The term "point mutation", as used herein, refers to the replacement of a single amino acid residue in the polypeptide chain of a protein product with a different amino acid residue.

The term, for example, "a G12V mutation", as used herein, refers to a point mutation which has resulted in the glycine (G) at position 12 of the wild-type RAS protein being replaced with valine (V). Similar definitions apply to similar terms, such as G13C, G13R, Q61H etc.

The term "pharmaceutical composition", as used herein, means a pharmaceutical preparation suitable for administration to an intended human or animal subject for therapeutic purposes.

BRIEF DESCRIPTION OF THE SEQUENCE LISTING

Figure 1:
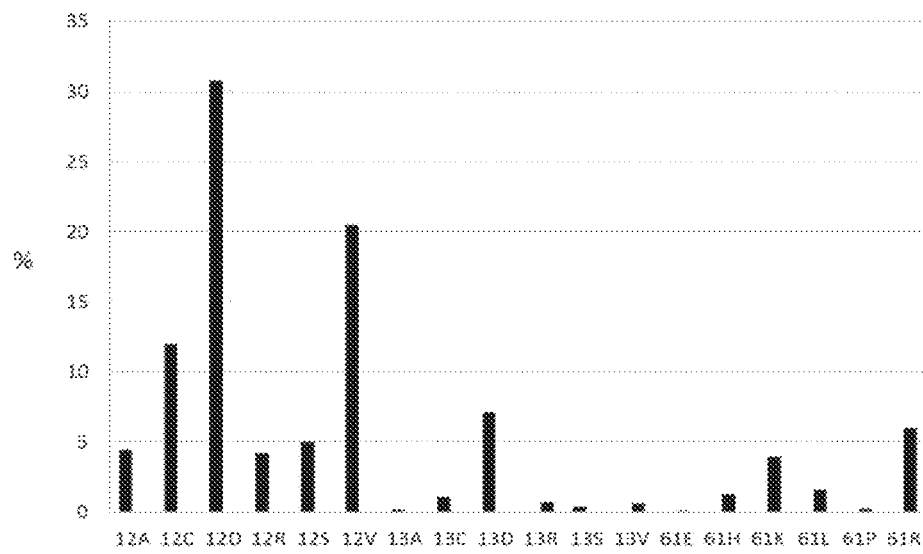
FIG. 1 is a graph showing the incidence of RAS mutations present in all cancers.

SEQ ID NO:1 shows an amino acid sequence of the RAS peptide having a G13C mutation.
SEQ ID NO:2 shows an amino acid sequence of the RAS peptide having a G13R mutation.
SEQ ID NO:3 shows an amino acid sequence of the RAS peptide having a G13D mutation.
SEQ ID NO:4 shows an amino acid sequence of the RAS peptide having a G13V mutation.
SEQ ID NO:5 shows an amino acid sequence of the RAS peptide having a G13A mutation.
SEQ ID NO:6 shows an amino acid sequence of the RAS peptide having a G13S mutation.
SEQ ID NO:7 shows an amino acid sequence of the RAS peptide having a G12A mutation.
SEQ ID NO:8 shows an amino acid sequence of the RAS peptide having a G12C mutation.
SEQ ID NO:9 shows an amino acid sequence of the RAS peptide having a G21D mutation.
SEQ ID NO:10 shows an amino acid sequence of the RAS peptide having a G12R mutation.
SEQ ID NO:11 shows an amino acid sequence of the RAS peptide having a G12S mutation.
SEQ ID NO:12 shows an amino acid sequence of the RAS peptide having a G12V mutation.
SEQ ID NO:13 shows an amino acid sequence of the RAS peptide having a Q61R mutation.
SEQ ID NO:14 shows an amino acid sequence of the RAS peptide having a Q61K mutation.
SEQ ID NO:15 shows an amino acid sequence of the RAS peptide having a Q61H mutation.
SEQ ID NO:16 shows an amino acid sequence of the RAS peptide having a Q61L mutation.
SEQ ID NO:17 shows an amino acid sequence of the RAS peptide having a Q61E mutation.
SEQ ID NO:18 shows an amino acid sequence of the RAS peptide having a Q61P mutation.
SEQ ID NO:19 shows an amino acid sequence of the RAS peptide of TG02 having a G13C mutation.
SEQ ID NO:20 shows an amino acid sequence of the RAS peptide of TG02 having a G13D mutation.
SEQ ID NO:21 shows an amino acid sequence of the RAS peptide of TG02 having a G12A mutation.
SEQ ID NO:22 shows an amino acid sequence of the RAS peptide of TG02 having a G12C mutation.
SEQ ID NO:23 shows an amino acid sequence of the RAS peptide of TG02 having a G12D mutation.
SEQ ID NO:24 shows an amino acid sequence of the RAS peptide of TG02 having a G12R mutation.
SEQ ID NO:25 shows an amino acid sequence of the RAS peptide of TG02 Having a G12S mutation.
SEQ ID NO:26 shows an amino acid sequence of the RAS peptide of TG02 having a G12V mutation.
SEQ ID NO:27 shows an amino acid sequence of the RAS peptide of TG03 having a G13R mutation.
SEQ ID NO:28 shows an amino acid sequence of the RAS peptide of TG03 having a G13V mutation.
SEQ ID NO:29 shows an amino acid sequence of the RAS peptide of TG03 having a Q61R mutation.
SEQ ID NO:30 shows an amino acid sequence of the RAS peptide of TG03 having a Q61K mutation,
SEQ ID NO:31 shows an amino acid sequence of the RAS peptide of TG03 having a Q61H mutation.
SEQ ID NO:32 shows an amino acid sequence of the RAS peptide of TG03 having a Q61L mutation.
SEQ ID NO:33 shows the full length amino acid sequence of the wild-type RAS protein.

DETAILED DESCRIPTION OF THE INVENTION

The invention relates, in general terms, to a peptide mixture comprising at least first and second peptides of the RAS protein comprising a region of at least 8 amino acids which includes position 13 of the RAS protein, wherein each of the at least first and second peptides has a point mutation at position 13, and wherein the position 13 mutations are different from each other.

The peptides in the mixture of the invention may be peptides to any of HRAS, KRAS or NRAS. All three of these RAS isoforms share sequence identity in all of the regions responsible for GDP/GTP binding, i.e. the regions subject to mutation in cancer.

In some embodiments, each of the first and second peptides independently comprises at least 8, at least 9, at least 10, at least 12, at least 16, at least 17, at least 18, at least 20, at least 24 or at least 30 amino acids. In preferred embodiments, each of the first and second peptides comprises at least 8 amino acids. In other preferred embodiments, each of the first and second peptides comprises at least 17 amino acids.

In some embodiments, each of the first and second peptides independently has no more than 30 amino acids. For example, each of the first and second peptides independently comprises no more than 28, 26, 24, 22, 20, 18, 17, 16, 14, 12, 10 or 8 amino acids in certain embodiments. In some embodiments, each of the first and second peptides comprises no more than 17 amino acids.

In some embodiments, each of the first and second peptides independently has at least 20%, at least 25%, at least 30%, at least 37%, at least 50%, at least 60%, at least 66%, at least 75%, at least 85%, at least 95%, at least 99% or 100% sequence identity at positions other than the region including position 13 with the RAS protein. In some embodiments, each of the first and second peptides independently has at least 20%, at least 25%, at least 30%, at least 40%, at least 50%, at least 60%, at least 66%, at least 75%, at least 85%, at least 95%, at least 99% or 100% sequence identity at positions other than the region including position 13 to one of SEQ ID NOs: 1-6. In preferred embodiments, each of the first and second peptides independently has at least 95% sequence identity at positions other than the region including position 13 to one of SEQ ID NOs: 1-6. In other embodiments, each of the first and second peptides independently has 100% sequence identity at positions other than the region including position 13 to one of SEQ ID NOs: 1-6. In some embodiments, the first peptide has a percentage sequence identity at positions other than the region including position 13 to one of SEQ ID NOs: 1-6 and the second peptide has a different percentage sequence identity at positions other than the region including position 13 to a different one of SEQ ID NOs: 1-6. In other embodiments, the first peptide has a percentage sequence identity at positions other than the region including position 13 to one of SEQ D NOs: 1-6 and the second peptide has the same percentage sequence identity at positions other than the region including position 13 to a different one of SEQ ID NOs; 1-6. In all embodiments each of the first and second peptides is capable of eliciting an immune response.

Each of the first and second peptides in the peptide mixture has a point mutation at position 13 of the RAS protein, wherein the point mutation in the first peptide is different from the point mutation in the second peptide. The wild-type RAS protein comprises glycine (G) at position 13. Thus, the mutation at position 13 may be a point mutation from glycine to any other amino acid. However, G13A, G13C, G13D, G13R, G13S and G13V mutations have been found to be particularly associated with cancer. Thus, in preferred embodiments, the point mutation of each of the first and second peptides is independently one of a G13A, G13C, G13D, G13R, G13S or a G13V mutation. In more preferred embodiments, the point mutation at position 13 of one of the first and second peptides is independently a G13C or a G13R mutation. In particularly preferred embodiments, the point mutation at position 13 of one of the first or second peptides is a G13C mutation. In other particularly preferred embodiments, the point mutation at position 13 of one of the first or second peptides is a G13R mutation.

In some embodiments, the point mutation at position 13 of the first or second peptide is a G13C mutation and the point mutation at position 13 of the other peptide is a G13D mutation.

In other embodiments, the point mutation at position 13 of the first or second peptide is a G13R mutation and the point mutation at position 13 of the other peptide is a G13V mutation.

In further embodiments, the point mutation at position 13 of the first or second peptide is a G13C mutation, and the point mutation at position 13 of the other peptide is a G13R mutation.

In alternative embodiments of the invention, the peptide mixture may comprise at least a third peptide of the RAS protein comprising a region of at least 8 amino acids including position 13 of the RAS protein. The at least third peptide may have a point mutation at the amino acid corresponding to position 13 of the RAS protein that is different to the position 13 mutations of the first and second peptides. The point mutation may be one of a. G13A, G13C, G13D, G13R, G13S or a G13V mutation, independently of the point mutations of the first and second peptides. In some embodiments, the first peptide has a G13C mutation, the second peptide has a G13D mutation and the third peptide has a G13R mutation.

The peptide mixture of the invention may additionally comprise at least one further peptide of the RAS protein comprising a region of at least 8 amino acids. In some embodiments, said region of the at least one further peptide includes position 12 of the RAS protein. In other embodiments, said region of the at least one further peptide includes position 61 of the RAS protein.

In embodiments where the peptide mixture comprises at least a third peptide, each of the peptides independently comprises at least 8, at least 9, at least 10, at least 12, at least 16, at least 17, at least 18, at least 20, at least 24 or at least 30 amino acids. In preferred embodiments, each of the peptides comprises at least 8 amino acids. In other preferred embodiments, each of the peptides comprises at least 17 amino acids. In further embodiments, each of the peptides comprises at least 18 amino acids. In general, each peptide in the peptide mixture may comprise a different number of amino acids to one or more of the other peptides in the peptide mixture. In some embodiments, each peptide in the peptide mixture comprises no more than 30 amino acids. For example, each peptide in the peptide mixture independently comprises no more than 28, 26, 24, 22, 20, 18, 17, 16, 14, 12, 10 or 8 amino acids in certain embodiments. In some embodiments, each peptide in the peptide mixture comprises not more than 17 amino acids.

In embodiments where the peptide mixture comprises at least one further peptide comprising a region including position 12 of the RAS protein, the amino acid corresponding to position 12 of the RAS protein has a point mutation. In the wild-type RAS protein, the amino acid of position 12 is glycine (G). Thus, in some embodiments, the point mutation at position 12 may be to an amino acid other than glycine. In some embodiments, each mutation is, independently, a G12A, G12C, G12D, G12R, G12S or a G12V mutation. In other embodiments, the at least one further peptide has at least 20%, at least 25%, at least 30%, at least 40%, at least 50%, at least 60%, at least 66%, at least 75%, at least 85%, at least 95%, at least 99% or 100% sequence identity at positions other than the region including position 12 with the RAS protein. In some embodiments, the at least one further peptide has at least 20%, at least 25%, at least 30%, at least 40%, at least 50%, at least 60%, at least 66%, at least 75%, at least 85%, at least 95%, at least 99% or 100% sequence identity at positions other than the region including position 12 to one of SEQ ID NO: 7-12 and 21-26. In some embodiments, there is more than one further peptide of the RAS protein comprising a region of at least 8 amino acids including position 12 of the RAS protein and having a point mutation at the amino acid corresponding to position 12 of the RAS protein. In such embodiments, each of the peptides having a position 12 mutation has a different point mutation.

In embodiments where the peptide mixture comprises at least one further peptide comprising a region of at least 8 amino acids including position 61 of the RAS protein, the amino acid corresponding to position 61 of the RAS protein has a point mutation. In the wild-type RAS protein, the amino acid at position 61 is glutamine (Q). Thus, in some embodiments, the point mutation at position 61 is to an amino acid other than glutamine. In some embodiments, the point mutation is a Q61E, Q61H, Q61K, Q61L, a Q61P or a Q61R mutation. In other embodiments, the at least one further peptide has at least 20%, at least 25%, at least 30%, at least 40%, at least 50%, at least 60%, at least 66%, at least 75%, at least 85%, at least 95%, at least 99% or 100% sequence identity at positions other than the region including position 61 with the RAS protein. In some embodiments, the at least one further peptide has at least 20%, at least 25%, at least 30%, at least 40%, at least 50%, at least 60%, at least 66%, at least 75%, at least 85%, at least 95%, at least 99% or 100% sequence identity at positions other than the region including position 61 to one of SEQ ID NO: 13-18 and 29-32. In some embodiments, there is more than one further peptide of the RAS protein comprising a region of at least 8 amino acids including position 61 of the RAS protein and having a point mutation at the amino acid corresponding to position 61 of the RAS protein. In such embodiments, each of the peptides having a position 61 mutation has a different point mutation.

In some embodiments, the peptide mixture further comprises at least two peptides of the RAS protein, each comprising a region of at least 8 amino acids including position 12 or 61 of the RAS protein. In such embodiments, the at least two further peptides comprise at least one peptide having a region of at least 8 amino acids including position 12 of the RAS protein, having a point mutation at the amino acid corresponding to position 12 of the RAS protein, and at least one peptide comprising a region of at least 8 amino acids including position 61 of the RAS protein, having a point mutation at the amino acid corresponding to position 61 of the RAS protein. The point mutation at position 12 may be one of a G12A, G12C, G12D, G12R, G12S or a G12V mutation. The point mutation at position 61 may be one of a Q61E, Q61H, Q61K, Q61L, a Q61P, or a Q61R mutation. The at least one peptide including position 12 of the RAS protein may have at least 20%, at least 25%, at least 30%, at least 40%, at least 50%, at least 60%, at least 66%, at least 75%, at least 85%, at least 95%, at least 99%, or 100% sequence identity at positions other than the region including position 12 with the RAS protein. In some embodiments, the at least one further peptide comprising a region of at least 8 amino acids including position 12 has at least 20%, at least 25%, at least 30%, at least 40%, at least 50%, at least 60%, at least 66%, at least 75%, at least 85%, at least 95%, at least 99% or 100% sequence identity at positions other than the region including position 12 to one of SEQ ID NOs: 7-12 and 21-26. The at least one peptide comprising a region of at least 8 amino acids including position 61 of the RAS protein may have at least 20%, at least 25%, at least 30%, at least 40%, at least 50%, at least 60%, at least 66%, at least 75%, at least 85%, at least 95%, at least 99% or 100% sequence identity at positions other than the region including position 61 with the RAS protein. In some embodiments, the at least one further peptide including position 61 of the RAS protein has at least 20%, at least 25%, at least 30%, at least 40%, at least 50%, at least 60%, at least 66%, at least 75%, at least 85%, at least 95%, at least 99% or 100% sequence identity at positions other than the region including position 61 to one of SEQ ID NOs: 13-18 and 29-32. Any combination of the above-mentioned mutations and SEQ ID NOs is envisaged in peptide mixtures of the present invention.

Figure 2:
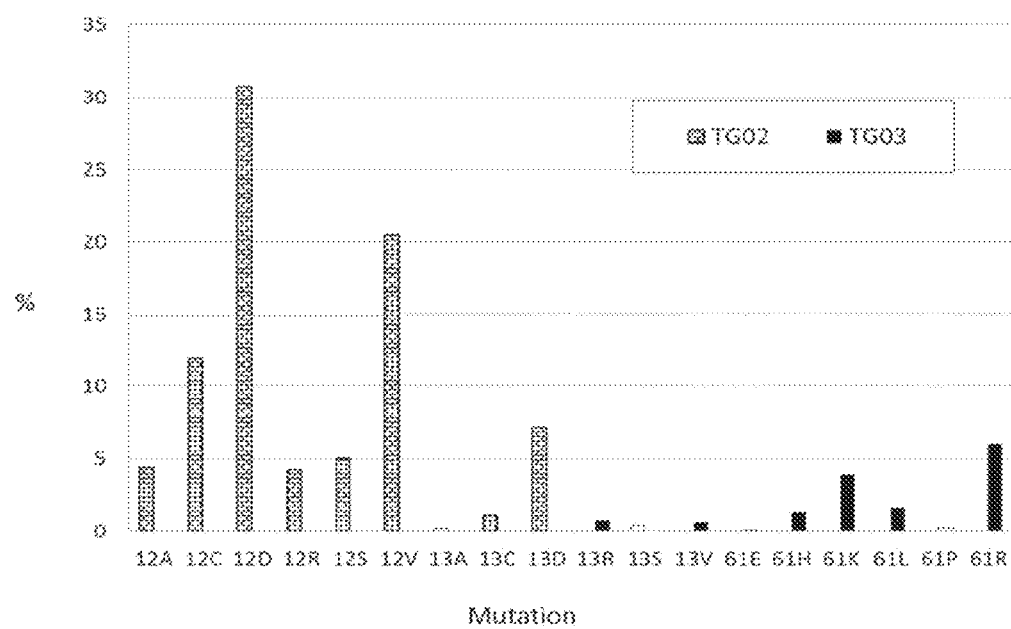
FIG. 2 is a graph showing the respective incidence of RAS mutations in all cancers corresponding to peptides in two peptide mixtures (TG02 and TG03) of the present invention.
Figure 3:
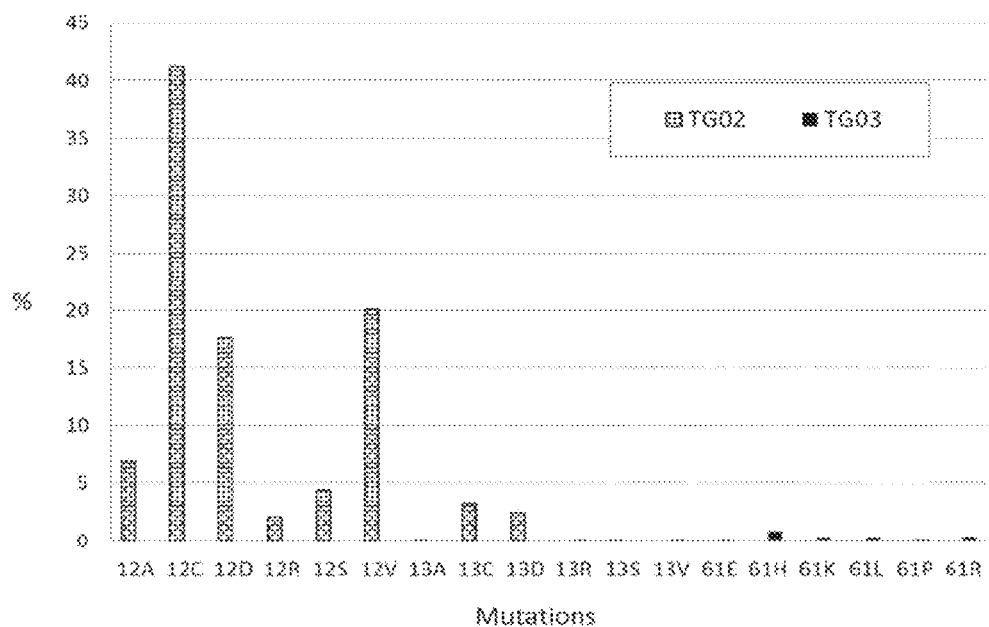
FIG. 3 is a graph showing the respective incidence of RAS mutations in lung cancer corresponding to peptides in two peptide mixtures (TG02 and TG03) of the present invention.
Figure 4:
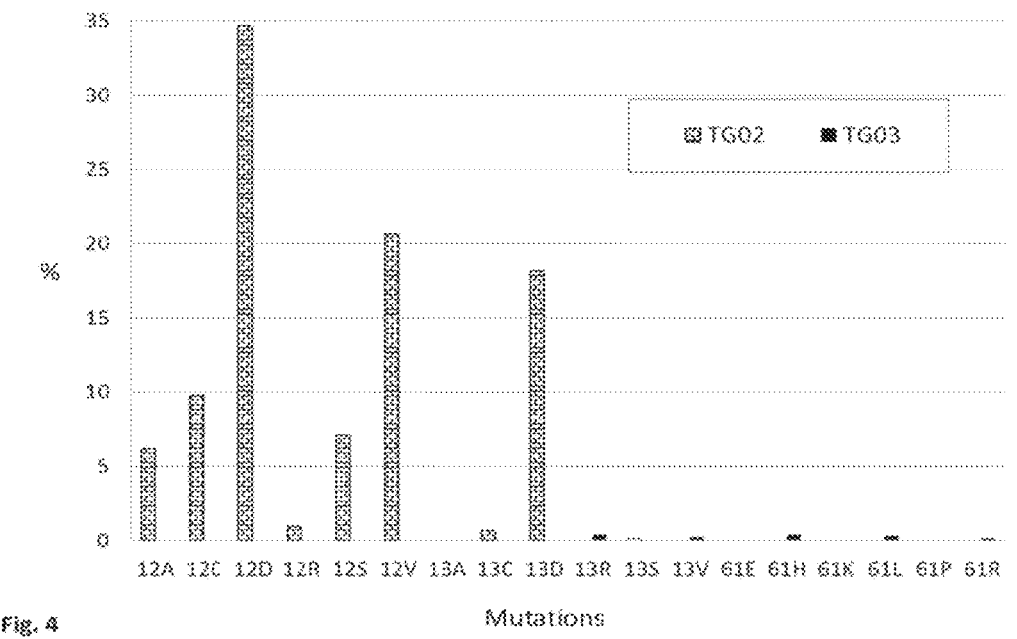
FIG. 4 is a graph showing the respective incidence of RAS mutations in colorectal cancer corresponding to peptides in two peptide mixtures (TG02 and TG03) of the present invention.
Figure 9:
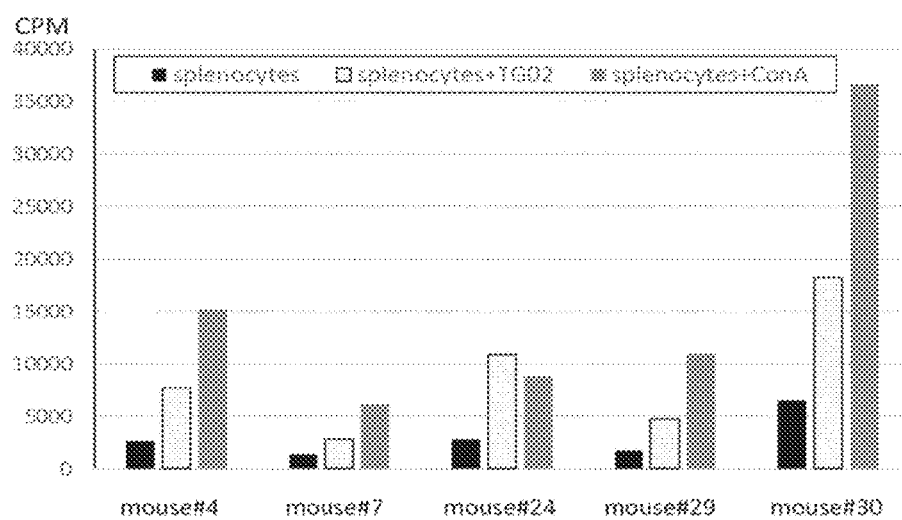
FIG. 9 is a graph showing the proliferative response of splenocytes harvested from mice vaccinated with a RAS peptide mixture (TG02; mouse #4 and #7) and TG02+ Viscogel™ (mouse #24, #29 and #30). ConA: Concanavalin A (positive control).

In some embodiments, the peptide mixture consists of a peptide having a G13C mutation, a peptide having a G13D mutation, a peptide having a G12A mutation, a peptide having a G12C mutation, a peptide having a G12D mutation, a peptide having a G12R mutation, a peptide having a G12S mutation, and a peptide having a G12V mutation. In such embodiments, the peptide mixture consists of peptides independently having at least 20%, at least 25%, at least 30%, at least 40%, at least 50%, at least 60%, at least 66%, at least 75%, at least 85%, at least 95%, at least 99% or 100% sequence identity at positions other than the region including positions 12 or 13 respectively to SEQ ID NOs: 1, 3, 7, 8, 9, 10, 11 and 12. In some embodiments, the peptide mixture consists of peptides independently having at least 20%, at least 25%, at least 30%, at least 40%, at least 50%, at least 60%, at least 66%, at least 75%, at least 85%, at least 95%, at least 99% or 100% sequence identity at positions other than the region including positions 12 or 13 respectively to SEQ ID NOs: 19-26. This embodiment of the invention is herein referred to as TG02 when there is 100% sequence identity to SEQ ID NOs: 19-26. Table 4 and FIG. 2 show the peptides which are preferably present in TG02. The incidence these mutations in cancers associated with a RAS mutation, lung cancer and colorectal cancer is shown in FIGS. 1, 3 and 4, respectively. The results of a splenocyte proliferation assay, following vaccination of mice with TG02, are shown in FIG. 9, and show that TG02 is effective in inducing an immune response.

Figure 5:
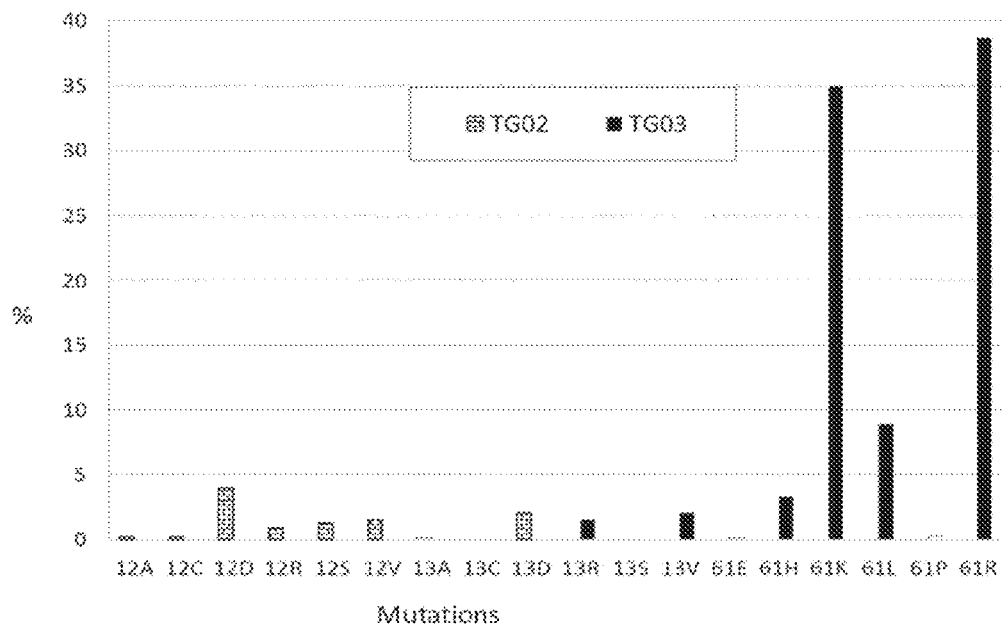
FIG. 5 is a graph showing the respective incidence of RAS mutations in malignant melanoma corresponding to peptides in two peptide mixtures (TG02 and TG03) of the present invention.

In alternative embodiments, the peptide mixture consists of a peptide having a G13R mutation, a peptide having a G13V mutation, a peptide having a Q61H mutation, a peptide having a Q61K mutation, a peptide having a Q61L mutation, and a peptide having a Q61R mutation. In such embodiments, the peptide mixture consists of peptides independently having at least 20%, at least 25%, at least 30%, at least 40%, at least 50%, at least 60%, at least 66%, at least 75%, at least 85%, at least 95%, at least 99% or 100% sequence identity at positions other than the region including positions 13 and 61 respectively to SEQ ID NOs: 2, 4, 13, 14, 15 and 16. In some embodiments, the peptide mixture consists of peptides independently having at least 20%, at least 25%, at least 30%, at least 40%, at least 50%, at least 60%, at least 66%, at least 75%, at least 85%, at least 95%, at least 99% or 100% at positions other than the region including position 13 or 61 respectively to SEQ ID NOs: 27-32. This embodiment of the invention is referred to herein as TG03 when there is 100% sequence identity to SEQ ID NOs: 27-32. Table 5 and FIG. 2 show the peptides of TG03. The incidence of these mutations in malignant melanoma is shown in FIG. 5.

Figure 7:
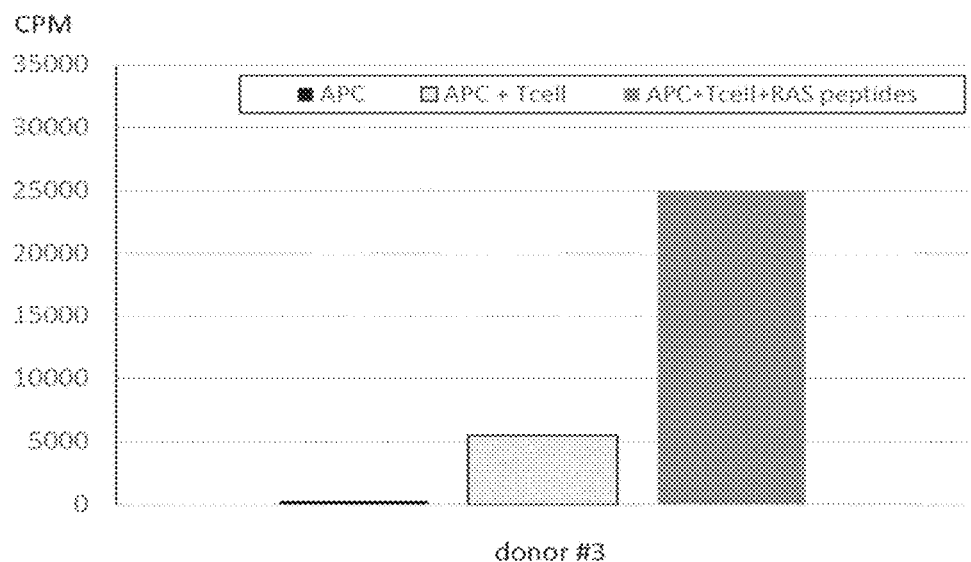
FIG. 7 is a graph showing the proliferative T cell response to three rounds of in vitro stimulation with a RAS peptide mixture consisting of a G13C peptide (SEQ ID NO: 19), a G13D peptide (SEQ ID NO: 20), a G12A peptide (SEQ ID NO: 21), a G12C peptide (SEQ ID NO: 22), a G12D peptide (SEQ ID NO: 23), a G12R peptide (SEQ ID NO: 24), a G12S peptide (SEQ ID NO: 25), a G12V peptide (SEQ ID NO: 26) and a G13R peptide (SEQ ID NO: 27), in a healthy donor. APC: antigen presenting cells (PBMC), CPM: counts per minute.

In other embodiments, the peptide mixture consists of a peptide having a G13C mutation, a peptide having a G13D mutation, a peptide having a G13R mutation, a peptide having a G12A mutation, a peptide having a G12C mutation, a peptide having a G12D mutation, a peptide having a G12R mutation, a peptide having a G12S mutation, and a peptide having a G12V mutation. In such embodiments, the peptide mixture consists of peptides independently having at least 20%, at least 25%, at least 30%, at least 40%, at least 50%, at least 60%, at least 66%, at least 75%, at least 85%, at least 95%, at least 99% or 100% sequence identity at positions other than the region including positions 12 or 13 respectively to SEQ ID NOs: 1, 2, 3, 7, 8, 9, 10, 11 and 12. In some embodiments, the peptide mixture consists of peptides independently having at least 20%, at least 25%, at least 30%, at least 40%, at least 50%, at least 60%, at least 66%, at least 75%, at least 85%, at least 95%, at least 99% or 100% sequence identity at positions other than the region including positions 12 or 13 respectively to SEQ ID NOs: 19-27. The results of a T cell proliferation assay following in vitro stimulation of PMBCs with this embodiment of the peptide mixture are shown in FIG. 7, and show that T cells were stimulated by this mixture. Thus, peptide mixtures of the invention are effective in inducing an immune response.

In general, peptides of the present invention, within a region of 8 amino acids including position 12, 13 or 61, have at least 6 amino acid residues, other than the residue at position 12, 13 or 61 respectively, which are identical to the corresponding region of the RAS protein. Furthermore, in general, peptides of the present invention, at positions other than the region including position 12, 13 or 61 of the RAS protein independently have at least 20%, at least 25%, at least 30%, at least 40%, at least 50%, at least 60%, at least 66%, at least 75%, at least 85%, at least 95%, at least 99% or 100% to one of SEQ ID NOs: 1-32, respectively.

In some embodiments, the peptide mixture consists of a first, second, third and fourth peptide, wherein the first and second peptides are as described above. Each of the third and fourth peptides comprises a region of at least 8 amino acids including position 13 of the RAS protein, and each of the third and fourth peptides independently has at least 20%, at least 25%, at least 30%, at least 40%, at least 50%, at least 60%, at least 66%, at least 75%, at least 85%, at least 95%, at least 99% or 100% sequence identity at positions other than the region including position 13 with the RAS protein. Each of the third and fourth peptides may independently have at least 20%, at least 25%, at least 30%, at least 40%, at least 50%, at least 60%, at least 66%, at least 75%, at least 85%, at least 95%, at least 99% or 100% sequence identity at positions other than the region including position 13 to one of SEQ ID NOs: 1-6, 19, 20, 27 or 28, Each of the third and fourth peptides has a point mutation at the amino acid corresponding to position 13 of the RAS peptide, and each of the first, second, third and fourth peptides has a point mutation that is different from the point mutations of the other peptides. In one embodiment, the first peptide is a peptide having a G13R mutation, the second peptide is a peptide having a G13A mutation, the third peptide is a peptide having a G13S mutation and the fourth peptide is a peptide having a G13V mutation.

In some embodiments, there is a maximum of 8 different peptides in the peptide mixture. In some embodiments, there is a maximum of 9 different peptides in the peptide mixture. In other embodiments, there is a maximum of 10, 12, 14, or 16 different peptides. In embodiments where the peptide mixture comprises at least one further peptide comprising a region including position 12 of the RAS protein, the peptide mixture comprises 1, 2, 3, 4, 5 or 6 peptides comprising a region of at least 8 amino acids including position 12 of the RAS peptide and having a point mutation at the position corresponding to position 12 of the RAS protein. In embodiments where the peptide mixture comprises at least one further peptide comprising a region of at least 8 amino acids including position 61 of the RAS protein, the peptide mixture comprises 1, 2, 3, 4, 5 or 6 peptides comprising a region including position 61 of the RAS protein and having a point mutation at the amino acid corresponding to position 61 of the RAS protein, wherein each of the peptides has a different point mutation.

In some embodiments, the peptides comprising a region of at least 8 amino acids including position 13 of the RAS peptide comprise positions 1 to 30 of the RAS protein. In alternative embodiments, the peptides comprising a region of at least 8 amino acids including position 13 of the RAS protein comprise positions 5 to 21 of the RAS protein. In further embodiments, the amino acid corresponding to position 13 of the RAS protein is at the C-terminus of the peptide. In further embodiments, the amino acid corresponding to position 13 of the RAS protein is at the N-terminus of the peptide. In general, the region having at least 8 amino acids including position 13 of the RAS protein may consist of any 8 positions of the RAS protein including position 13. For example, the region having at least 8 amino acids including position 13 may consist of the amino acids from position 6 to position 13, position 7 to position 14, position 8 to position 15, position 9 to position 16, position 10 to position 17, position 11 to position 18, position 12 to position 19 or position 13 to position 20 of the RAS protein.

In some embodiments, the peptides comprising a region of at least 8 amino acids including position 12 of the RAS peptide comprise positions 1 to 30 of the RAS protein. In other embodiments, the peptides comprising a region of at least 8 amino acids including position 12 of the RAS protein comprises positions 5 to 21 of the RAS protein. In alternative embodiments, the amino acid corresponding to position 12 of the RAS protein is at the C-terminus of the peptide. In further embodiments, the amino acid corresponding to position 12 of the RAS protein is at the N-terminus of the peptide. In general, the region having at least 8 amino acids including position 12 of the RAS protein may consist of any 8 positions of the RAS protein including position 12. For example, the region having at least 8 amino acids including position 12 may consist of the amino acids from position 5 to position 12, position 6 to position 13, position 7 to position 14, position 8 to position 15, position 9 to position 16, position 10 to position 17, position 11 to position 18 or position 12 to position 19 of the RAS protein.

In some embodiments, the peptides comprising a region of at least 8 amino acids including position 61 of the RAS peptide comprise positions 47 to 76 of the RAS protein. In other embodiments, the peptides comprising a region of at least 8 amino acids including position 61 of the RAS peptide comprise positions 53 to 69 of the RAS protein. In alternative embodiments, the amino acid corresponding to position 61 of the RAS protein is at the C-terminus of the peptide. In further embodiments, the amino acid corresponding to position 61 of the RAS protein is at the N-terminus of the peptide. In general, the region having at least 8 amino acids including position 61 of the RAS protein may consist of any 8 positions of the RAS protein including position 13. For example, the region having at least 8 amino acids including position 61 may consist of the amino acids from position 54 to position 61, position 55 to position 62, position 56 to position 63, position 57 to position 64, position 58 to position 65, position 59 to position 66, position 60 to position 67 or position 61 to position 68 of the RAS protein.

The peptide mixtures of the present invention may contain the peptides in equal or in different proportions. In some embodiments, the first and second peptides are present in the mixture in equal proportions, i.e. each peptide comprises 50% of the peptide component of the peptide mixture. In other embodiments, there is a greater proportion of the first peptide in the peptide mixture than the second peptide. For example, the first peptide may comprise at least 55%, at least 60%, at least 70%, at least 80% or at least 90% of the peptide component of the peptide mixture. In alternative embodiments, there is a greater proportion of the second peptide in the peptide mixture than the first peptide. For example, the second peptide may comprise at least 55%, at least 60%, at least 70%, at least 80% or at least 90% of the peptide component of the peptide mixture. In embodiments comprising at least one further peptide, the peptides are present in the peptide component of the peptide mixture in equal proportions. In other embodiments, the first, second and the at least one further peptide are present in different proportions from each other. For example, each of the first, second and at least one further peptide may independently comprise at least 1%, at least 5%, at least 10%, at least 20% at least 30%, at least 40%, at least 50%, at least 60%, at least 60%, at least 70%, at least 80% or at least 90% of the peptide component of the peptide mixture.

Alternative embodiments include a peptide mixture comprising at least five peptides of the RAS protein wherein each of the five peptides comprises a region of at least 8 amino acids including position 13 of the RAS protein. Each of the at least five peptides independently has at least 20%, at least 25%, at least 30%, at least 40%, at least 50%, at least 60%, at least 66%, at least 75%, at least 85%, at least 95%, at least 99% or 100% sequence identity at positions other than the region including position 13 with the RAS protein, and/or independently has at least 20%, at least 25%, at least 30%, at least 40%, at least 50%, at least 60%, at least 66%, at least 75%, at least 85%, at least 95%, at least 99% or 100% sequence identity at positions other than the region including position 13 to one of SEQ ID NOs: 1-6, 19, 20, 27 and 28. Each of the at least five peptides has a point mutation at the amino acid corresponding to position 13 of the RAS protein, independently selected from a G13A, G13C, G13D, G13R, G13S or a G13V mutation, and the point mutation of each peptide is different from the point mutation of the other peptides.

In another embodiment, the peptide mixture suitable for eliciting an immune response consists of six peptides of the RAS protein wherein each peptide comprises a region of at least 8 amino acids including position 12 of the RAS protein. Each of the peptides independently has at least 20%, at least 25%, at least 30%, at least 40%, at least 50%, at least 60%, at least 66%, at least 75%, at least 85%, at least 95%, at least 99% or 100% sequence identity at positions other than the region including position 12 with the RAS protein, and/or independently has at least 20%, at least 25%, at least 30%, at least 40%, at least 50%, at least 60%, at least 66%, at least 75%, at least 85%, at least 95%, at least 99% or 100% sequence identity at positions other than the region including position 12 to one of SEQ ID NOs: 7-12 and 21-26. Each of the peptides has a point mutation at the amino acid corresponding to position 12 of the RAS protein, which is selected from a G12A, G12C, G12D, G12R, G12S or a G12V mutation, and the point mutation of each peptide is different from the point mutation of the other peptides.

In a further embodiment, a peptide mixture suitable for eliciting an immune response consists of a first, second, third and fourth peptide of the RAS protein wherein each of the first, second and third peptides comprises a region of at least 8 amino acids including position 12 of the RAS protein, and the fourth peptide of the RAS protein comprises a region of at least 8 amino acids including position 13 of the RAS protein. Each of the first, second, third and fourth peptides independently has at least 20%, at least 25%, at least 30%, at least 40%, at least 50%, at least 60%, at least 66%, at least 75%, at least 85%, at least 95%, at least 99% or 100% sequence identity at positions other than the region including position 12 or 13 respectively with the RAS protein, and/or independently has at least 20%, at least 25%, at least 30%, at least 40%, at least 50%, at least 60%, at least 66%, at least 75%, at least 85%, at least 95%, at least 99% or 100% sequence identity at positions other than the region including position 12 or 13 respectively to one of SEQ ID NOs: 7-12, 21-26, 1-6, 19, 20, 27 and 28 respectively. Each of the first, second, third and fourth peptides has a point mutation at the amino acid corresponding to said position 12 or 13 of the RAS protein, respectively. In some embodiments, the first peptide is a peptide having a G12A mutation, the second peptide is a peptide having a G12R mutation, the third peptide is a peptide having a G12S mutation, and the fourth peptide is a peptide having a G13C mutation.

In another aspect of the present invention, there is provided a peptide suitable for eliciting an immune response which corresponds to a fragment of the RAS protein. The peptide comprises a region of at least 8 amino acids which includes position 13 of the RAS protein, and the region of at least 8 amino acids has at least 6 amino acid residues, other than at position 13, which are identical to the corresponding region of the RAS protein. The peptide has a point mutation at the amino acid corresponding to position 13 of the RAS protein which is one of a G13C or a G13R mutation. In some embodiments, the peptide has a G13C mutation. In other embodiments, the peptide has a G13R mutation. Stimulation of T cells with such a peptide induced a proliferative response (FIG. 8), indicating that peptides according to this aspect of the invention are capable of inducing an immune response. In some embodiments, the peptide corresponding to a fragment of the RAS protein, and which comprises a region of at least 8 amino acids including position 13 of the RAS protein, comprises no more than 30 amino acid residues. For example, the peptide comprises no more than 28, 26, 24, 22, 20, 18, 17, 16, 14, 12, 10 or 8 amino acids in certain embodiments. In some embodiments, the peptide comprises no more than 17 amino acids.

In a further embodiment, there is provided a peptide for use as a vaccine or medicament. The peptide corresponds to a fragment of the RAS protein and comprises a region of at least amino acids including position 13 of the RAS protein. The region of at least 8 amino acids has at least 6 amino acid residues, other than at position 13, which are identical to the corresponding region of the RAS protein. The peptide for use as a vaccine or medicament has a point mutation at the amino acid corresponding to position 13 of the RAS protein which is one of a G13C or a G13R mutation.

Figure 6:
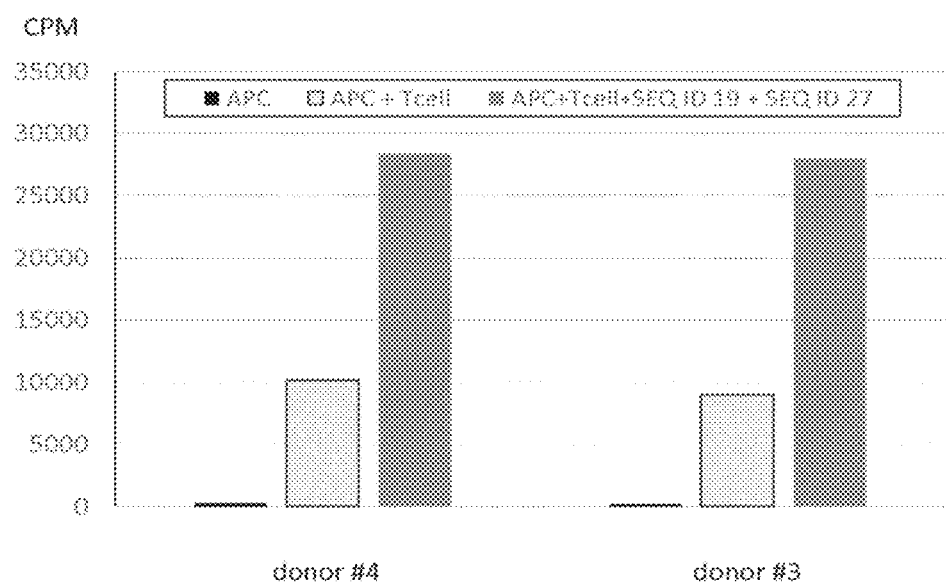
FIG. 6 is a graph showing the proliferative T cell response to three rounds of in vitro stimulation with a mixture of a RAS peptide having a G13C mutation (SEQ ID NO: 19) and a RAS peptide having a G13R mutation (SEQ ID NO: 27), in healthy donors. APC: antigen presenting cells (PBMC), CPM: counts per minute.
Figure 8:
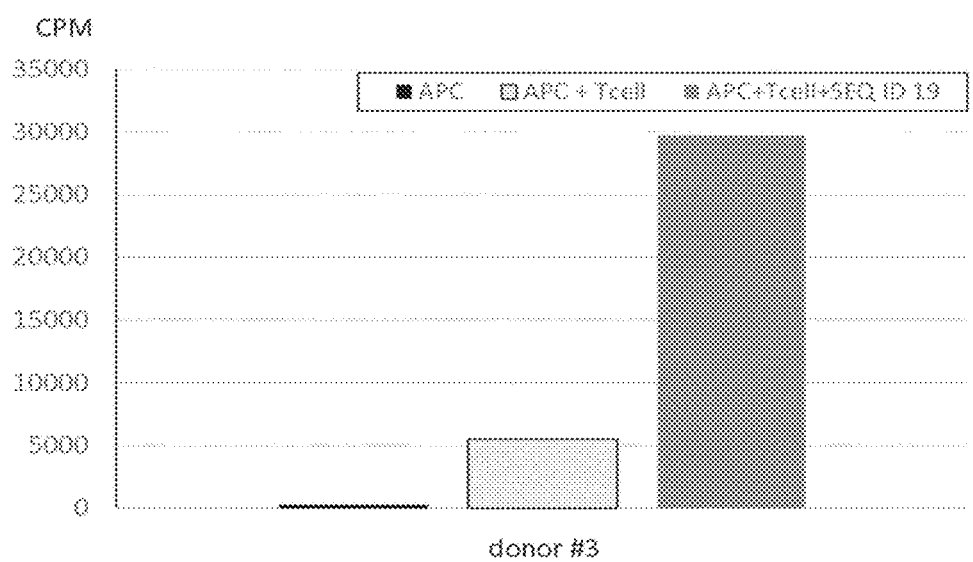
FIG. 8 is a graph showing the T cell response to G13C RAS peptide (SEQ ID NO: 19) after three rounds of in vitro stimulation with TG02+13R, in a healthy donor. APC: antigen presenting cells (PBMC), CPM: counts per minute.

The peptides of the present invention are peptides which correspond to the RAS protein fragments displayed by MHC II molecules on the surface of cells. Thus, the peptides of the present invention are peptides which correspond to the protein fragments which result from the intracellular proteolytic degradation of RAS proteins, which can then be displayed on HLA molecules, and to which individuals generally have a reactive T cell in their T cell repertoire. As shown in FIGS. 6-8, peptide mixtures and peptides in accordance with embodiments of the present invention induced a T cell proliferative response, while vaccination of mice with peptide mixtures of embodiments of the invention induced splenocyte proliferation (FIG. 9).

In a further aspect of the present invention, there is provided a T-cell mixture comprising T-cells specific for each of the peptides in one of the peptide mixtures according to the disclosures above, or a T-cell preparation comprising T-cells specific for a peptide according to the disclosures above, when presented on an MHC molecule. The T-cell mixture or preparation may be produced by stimulating at least one reactive T-cell with a peptide mixture comprising a first and a second peptide of the RAS protein, or a peptide of the RAS protein. For example, in one embodiment, the T-cell mixture comprises a plurality of T-cells wherein a first and a second T-cell are specific for a first and a second peptide, respectively, corresponding to a fragment of the RAS protein, wherein each peptide comprises a region of at least 8 amino acids including position 13 of the RAS protein, wherein each of the first and second T-cells is specific for a point mutation at the amino acid of the peptide corresponding to said position 13 and the point mutation for which the first T-cell is specific is different from the point mutation for which the second T-cell is specific. In another embodiment, for example, the T-cell preparation comprises a plurality of T-cells specific for a peptide corresponding to a fragment of the RAS protein, wherein the peptide comprises a region of at least 8 amino acids including position 13 of the RAS protein, wherein each T-cell is specific for a point mutation at the amino acid of the peptide corresponding to said position 13.

Peptide mixtures, peptides, T-cell mixtures and T-cell preparations of the present invention are for use in the treatment and/or prophylaxis of cancer, and in particular cancers associated with mutations in RAS oncogene. Cancers may include adrenal gland, autonomic ganglia, biliary tract, bone, breast, central nervous system, cervical, colorectal, endometrial, haematopoietic, lymphoid, kidney, large intestine, liver, lung, oesophagus, ovarian, pancreatic, prostate, salivary gland, skin, small intestine, stomach, testicular, thymus, thyroid, upper aerodigestive tract and urinary tract cancer, and malignant melanoma and the peptide mixtures, peptides, T-cell mixtures and T-cell preparations of the present invention may be used for the prophylaxis and/or treatment of more than one of these types of cancer. In some embodiments, a peptide mixture of the present invention wherein one of the first and second peptides has a G13C mutation, a peptide of the present invention wherein the peptide has a G13C mutation, a T-cell mixture wherein one of the first and second T-cells is specific for a peptide having a G13C mutation or a T-cell preparation wherein the T-cells are specific for a peptide having a G13C mutation, is for use in the prophylaxis and/or treatment of cancer. In such embodiments, it is preferred that the cancer is one or more of colorectal, lung and pancreatic cancer. In another embodiment, a peptide mixture of the present invention wherein one of the first and second peptides has a G13R mutation, a peptide of the present invention wherein the peptide has a G13R mutation, a T-cell mixture wherein one of the first or second T-cells is specific for a peptide having a G13R mutation or a T-cell preparation wherein the T-cells are specific for a peptide having a G13R mutation, may be used in the prophylaxis and/or treatment of cancer. In such embodiments, it is preferred that the cancer is malignant melanoma. In particular, it has been found that the peptide mixture referred to as TG02 covers 99% of cancers associated with mutations in RAS protein such that it has a broad spectrum of usage, while the peptide mixture referred to as TG03 covers 14% of cancers associated with mutations in RAS protein. Thus, in one embodiment, TG02 may be used in the prophylaxis and/or treatment of cancer. In preferred embodiments, the cancer is one or more of lung cancer, colorectal cancer and pancreatic cancer. In another embodiment, TG03 may be used in the prophylaxis or treatment of cancer. In preferred embodiments, the cancer is malignant melanoma.

Pharmaceutical compositions comprising the peptide mixtures, peptides, T-cell mixtures or T-cell preparations described above are also provided. Such pharmaceutical compositions may also comprise at least one pharmaceutically acceptable carrier, diluent and/or excipient. In some embodiments, the pharmaceutical composition further comprises one or more additional active ingredients and/or adjuvants. In certain embodiments the pharmaceutical composition may further comprise one or more ingredients therapeutically effective for the same disease indication. In one embodiment, the pharmaceutical composition of the present invention may further comprise one or more further chemotherapeutic agents, one or more antibodies, one or more small molecules and/or one or more immune stimulants (for example, cytokines). In some embodiments, the peptide mixture or the pharmaceutical composition may be used in combination with other forms of immunotherapy. As shown in FIG. 9, vaccination with a peptide mixture in accordance with an embodiment of the present invention induced splenocyte proliferation, indicating that peptides of the present invention are able to induce an immune response.

It has been found that certain types of cancer are associated with certain mutations of the RAS protein, and it has more recently been found that G13C and G13R mutations are differentially associated with cancer, such that G13C mutations are more commonly found in some types of cancer while G13R mutations are more commonly found in other types of cancer. Thus, it is possible to tailor the peptide mixtures, peptides, T-cell mixtures and T-cell preparations to target certain types of cancer. Thus, the present invention provides the advantage that vaccines and treatments are more specific to the patient's type of cancer. This means that fewer peptides and T-cells are needed in order to ensure that the vaccine and/or treatment is effective, which provides the advantage that fewer irrelevant peptides and/or T-cells are included in the vaccine and/or treatment. In turn, this reduces the problem of immunodominance, as there are fewer peptides which can compete with each other internally. Furthermore, the reduced number of required peptides and/or T-cells means that the pharmaceutical drugs and treatments are cheaper to produce.

The peptide mixture, peptide, or pharmaceutical composition of the invention may be administered to a subject by any suitable delivery technique known to those skilled in the art. For example, among other techniques, the peptide mixture, peptide or pharmaceutical composition may be administered to a subject by injection, in the form of a solution, in the form of liposomes or in dry form (for example, in the form of coated particles, etc). In some embodiments, the peptide mixture, peptide or pharmaceutical composition may be administered in an amount, for example, of between 1 µg and 1 g of each peptide once every three days, once a week, once a month, once every three months, once every four months or once every six months.

The T-cell mixtures and T-cell preparations of the present invention may be administered by intra-venous injection and/or infusion, and may be administered in an amount, for example, of between $10^6$ and $10^{12}$ of each T-cell specific for a peptide of the peptide mixture or peptide once every month, once every two months, once every three months, once every six months or once a year. Preferably, the dosage is administered once every month for between 2 and 5 months and is subsequently administered less frequently.

As mentioned above, the finding that different types of cancer are associated with different mutations of the RAS protein means that vaccines and treatments can be targeted to specific cancers. Thus, in another aspect of the invention, there is provided a peptide mixture, peptide, T-cell mixture and/or T-cell preparation for use in a method comprising the diagnosis of cancer and the selection of an appropriate treatment. The method comprises the steps of a) identifying the RAS protein point mutations present in a sample taken from a patient, and b) selecting a peptide mixture as described above comprising a peptide, selecting a peptide as described above, selecting a T-cell mixture as described above comprising a T-cell specific for a peptide and/or selecting a T-cell preparation as described above comprising a T-cell specific for a peptide, comprising a point mutation corresponding to at least one of the RAS protein point mutations identified in the sample. For example, if the sample taken from the subject were found to contain RAS proteins having a G13C mutation, a peptide mixture comprising a peptide, a peptide, and/or a T-cell mixture and/or preparation comprising a T-cell specific for a peptide, comprising a G13C mutation would be selected. In situations where the sample contains, for example, RAS proteins comprising a G13C mutation and a G12R mutation, a peptide mixture comprising a peptide comprising a G13C mutation and a peptide comprising a G12R mutation and/or a T-cell mixture comprising a T-cell specific for a peptide comprising a G13C mutation and a T-cell specific for a peptide comprising a G12R mutation, is selected. The method may also comprise the step of administering a pharmaceutical composition comprising the selected peptide mixture, peptide and/or T-cell mixture and/or preparation to the patient.

In further aspects of the invention, there is provided a kit that includes a peptide mixture, a peptide, a T-cell mixture and/or a T-cell preparation as described herein. The peptide mixture, peptide, T-cell mixture and/or T-cell preparation as such may be present in the kit, or the peptide mixture, peptide, T-cell mixture and/or T-cell preparation may be present in the kit as a pharmaceutical formulation. In some embodiments, the peptide mixture, peptide, T-cell mixture and/or T-cell preparation may be packaged, for example in a vial, bottle, flask, which may be further packaged, for example, within a box, envelope or bag. In some embodiments, the kit comprises a peptide mixture and/or a T-cell mixture wherein the peptides and/or the T-cells are provided in separate containers, such that the peptides and/or T-cells are mixed by the user.

Tables

TABLE 1

Position 13 mutated RAS peptides of SEQ ID NOs: 1-6

| | |
|---|---|
| 1             13               30 | |
| MTEYKINVVGAGCVGKSALTIQLIQNHFVD | (SEQ ID NO: 1) |
| MTEYKLVVVGAGRVGKSALTIQLIQNHFVD | (SEQ ID NO: 2) |
| MTEYKINVVGAGDVGKSALTIQLIQNHFVD | (SEQ ID NO: 3) |
| MTEYKLVVVGAGVVGKSALTIQLIQNHFVD | (SEQ ID NO: 4) |
| MTEYKLVVVGAGAVGKSALTIQLIQNHFVD | (SEQ ID NO: 5) |
| MTEYKLVVVGAGSVGKSALTIQLIQNHFVD | (SEQ ID NO: 6) |

TABLE 2

Position 12 mutated RAS peptides of SEQ ID NOs: 7-12

| | |
|---|---|
| 1            12              30 | |
| MTEYKLVVVGAAGVGKSALTIQLIQNHFVD | (SEQ ID NO: 7) |
| MTEYKLVVVGACGVGKSALTIQLIQNHFVD | (SEQ ID NO: 8) |
| MTEYKLVVVGADGVGKSALTIQLIQNHFND | (SEQ ID NO: 9) |
| MTEYKLVVVGARGVGKSALTIQLIQNHFVD | (SEQ ID NO: 10) |
| MTEYKLVVVGASGVGKSALTIQLIQNHFVD | (SEQ ID NO: 11) |
| MTEYKLVVVGAVGVGKSALTIQLIQNHFVD | (SEQ ID NO: 12) |

TABLE 3

Position 61 mutated RAS peptides of SEQ ID NOs: 13-18

| | |
|---|---|
| 47           61           76 | |
| DGETCLLDILDTAGREEYSAMRDQYMRTGE | (SEQ ID NO: 13) |
| DGETCLIDILDTAGKEEYSAMRDQYMRTGE | (SEQ ID NO: 14) |
| DGETCLLDILDTAGHEEYSAMRDQYMRTGE | (SEQ ID NO: 15) |
| DGETCLLDILDTAGLEEYSAMRDQYMRTGE | (SEQ ID NO: 16) |
| DGETCLIDILDTAGEEEYSAMRDQYMRTGE | (SEQ ID NO: 17) |
| DGETCLLDILDTAGPEEYSAMRDQYMRTGE | (SEQ ID NO: 18) |

TABLE 4

Peptides contained in TG02

| | |
|---|---|
| 5           21 | |
| KLVVVGAGCVGKSALTI | (SEQ ID NO: 19) |
| KLVVVGAGDVGKSALTI | (SEQ ID NO: 20) |
| KLVVVGAAGVGKSALTI | (SEQ ID NO: 21) |
| KLVVVGACGVGKSALTI | (SEQ ID NO: 22) |
| KLVVVGADGVGKSALTI | (SEQ ID NO: 23) |
| KLVVVGARGVGKSALTI | (SEQ ID NO: 24) |
| KLVVVGASGVGKSALTI | (SEQ ID NO: 25) |
| KLVVVGAVGVGKSALTI | (SEQ ID NO: 26) |

TABLE 5

Peptides contained in TG03

| | |
|---|---|
| 5           21 | |
| KLVVVGAGRVGKSALTI | (SEQ ID NO: 27) |
| KLVVVGAGVVGKSALTI | (SEQ ID NO: 28) |
| 53          69 | |
| LDILDTAGREEYSAMRD | (SEQ ID NO: 29) |
| LDILDTAGKEEYSAMRD | (SEQ ID NO: 30) |
| LDILDTAGHEEYSAMRD | (SEQ ID NO: 31) |
| LDILDTAGLEEYSAMRD | (SEQ ID NO: 32) |

EXAMPLES

Example 1

In this example, Buffy coats were collected from 4 normal human donors (Buffy 1, Buffy 2, Buffy 3, and Buffy 4) and were cultured in vitro. The in vitro PBMCs were stimulated with a single RAS peptide or a mixture of RAS peptides, and T cell proliferation assays performed. The results are shown in FIGS. 6-8.

Method

Equipment/Reagents

Hettich Rotina 420 (radius 210) or equivalent

KOJAIR Silverline Blue Series laminar flow hood or equivalent $CO_2$ incubator, Forma Scientific Model 3111 or equivalent Water bath 37° C.

KOVA Glasstic slide (Cat No. 87144E, Hycor Biomedical Inc, Garden Grove, USA)

TopCount, Microplate scintillation counter (Packard Instrument Company, Meriden, USA)

Cell Harvester Filtermate 196 Harvester, (Packard Instrument Company, Meriden, USA)

Unifilter GF/C (Cat.No. 6-005174, Nerliens Meszansky, Oslo, Norway) or equivalent Microscint-0 scintillation liquid (Cat. No. 6013611, Nerliens Meszansky, Oslo, Norway) or equivalent Topseal-A (Cat. No. 6005185, Nerliens Meszansky, Oslo, Norway) or equivalent $^3$H-Thymidine (Cat No. ART178-D, Nerliens Meszansky, Oslo, Norway) or equivalent CellGro DC medium (Cat. No. 0020801-0500, CellGenix GmbH, Freiburg, Germany) or equivalent RPMI-1640 (Cat No: E15-840) PAA Labs, Linz, Austria) or equivalent Dimethylsulfoxide (DMSO) (Cat No: D5879-500ML, Sigma-Aldrich Norway AS, Oslo, Norway) or equivalent Mucomyst (Cat.No. 019249, Meda AS, Asker, Norway) or equivalent Recombinant human interleukin-2 (IL-2, Proleukin®), (Chiron Therapeutics, Emeryville, USA) or equivalent
4-(2-hydroxyethyl)-1-piperazineethanesulfonic acid (HEPES) buffer 1 M (Cat. No. S11-001, Fisher Scientific AS, Oslo, Norway) or equivalent
IL-7 (Cat No. 207-IL-025, R & D Systems Europe Ltd, Abingdon, UK) or equivalent
Gentamucin 40 mg/ml (Cat. No. Sanofi Aventis Norge AS, Lysaker, Norway) or equivalent
Human Serum Albumin 20%, (Cat. No SW2G0013, Baxter AS, Oslo, Norway) or equivalent
24-well tissue culture plates (Cat. No. 734-1605, VWR international AS, Oslo, Norway) or equivalent
Microplate 96-well, round bottomed (Cat. No. 734-1797, VWR International AS, Oslo, Norway) or equivalent
Staphylococcal enterotoxin type C (SEC-3) (Cat. No. CT333, Toxin Technology Inc, Sarasota, USA).

Complete CellGro DC Medium Used for Culture:

The following was added to 500 ml of CellGro DC medium for the final concentrations:

Gentamicin 50 µg/ml (add 630 µL of 40 mg/ml stock to 500 mL medium)

Mucomyst 1.6 mg/ml (add 4 mL of 200 mg/ml stock to 500 mL medium)

HEPES buffer 0.01 M (add 5 ml of 1 M stock to 500 mL of medium)

Procedure a. Thawing of Frozen PBMC

The procedure must be performed at room temperature until point 5. All handling of cells in the open is done in a vertical laminar flow hood.

1. Rapidly transfer the vials, each vial with frozen PBMC from a buffy coat (Buffy 1, Buffy 2, Buffy 3, and Buffy 4), to a water bath at 37° C.
2. Shake the vials manually at regular intervals (approx. 2-3 min.) and remove them from the water bath while some ice is still present.
3. When all the ice is melted, transfer 1 ml of CellGro DC medium drop-wise to the cell suspension.
4. Transfer the cell suspension to a 50 ml tube containing 20 ml of CellGro DC medium.
5. Centrifuge cells at 500 G for 5 min at room temperature.
6. Resuspend the cells in 5 ml CellGro DC medium.
7. Count the number of viable cells using a Bürker chamber or KOVA Galsstic slides and adjust the cell concentration to $2\times10^6$ cells/ml in complete CellGro DC medium (see recipe). Total cell numbers: Buffy 1–$45\times10^6$, Buffy 2–$27.5\times10^6$, Buffy 3–$40.5\times10^6$, and Buffy 4–$40.5\times10^6$ cells.

b. Bulk Cultures for Increasing Number of RAS Peptide Reactive T Cells

1. Transfer 1 ml of thawed PBMCs ($2\times10^6$ cells/ml in DC medium) to each well in a 24-well plate.

TABLE 6

Re-stimulation: Number of wells stimulated with the peptide mixes.

| | Total number of cells (mill) | Peptide mix: 13C + 13R | Peptide mix: 13R + TG02-mix |
|---|---|---|---|
| Buffy 1 | 45 | 11 | 11 |
| Buffy 2 | 27.5 | 6 | 6 |
| Buffy 3 | 40.5 | 10 | 10 |
| Buffy 4 | 40.5 | 10 | 10 |

2. Add 20 µl of each of the 13C and 13R peptides, or 20 µl 13R and 60 µl TG02-mix to the wells for a final concentration of 10 µM of each peptide.
3. Culture the cells in a humidified incubator at 37° C./5% $CO_2$ for 3 days
4. Day 3: Add a final concentration of 2.0 iU/ml of recombinant human interleukin-2 (rIL-2) (i.e. 50 µl from stock solution of 1000 iU/ml and final concentration of 5 ng/ml recombinant human IL-7 (i.e. 10 µl from stock solution of 500 µg/ml) to the cell cultures and continue incubation at 37° C./5% $CO_2$. This step is optional if the cells are growing well.
5. Day 4-6: Cells are checked regularly under the microscope and split when required (500 µl was withdrawn from each well and replaced with 500 µl fresh CellGro DC medium, supplemented with 40 iU/ml IL-2 and IL-7).
6. Day 7-14: Cells are checked each day and wells with slow growing cells are mixed together.

c. i) 3-Days T Cell Proliferation Assay

1. Harvest, wash and count T cells in the bulk cultures from step b.;

TABLE 7

| | Total T cell numbers | |
|---|---|---|
| | Peptide mix: 13C + 13R | Peptide mix: 13R + TG02-mix |
| Buffy 1 | $0.9 \times 10^6$ | $0.72 \times 10^6$ |
| Buffy 2 | $5.0 \times 10^6$ | $4.05 \times 10^6$ |
| Buffy 3 | $7.65 \times 10^6$ | $7.2 \times 10^6$ |
| Buffy 4 | $6.3 \times 10^6$ | $2.7 \times 10^6$ |

2. Transfer $5\times10^4$ T cells from bulk cultures per well in round-bottomed 96-well plates.
3. Thaw 1 vial of autologous PBMCs sample in CellGro DC medium. Irradiate PBMCs (30 Gy), count and add $5\times10^4$ cells to each well and adjust to a total volume of 200 µl well with DC medium.
4. Prepare the following samples in triplicates, according to plate layout:
Negative controls:
T cells only
T-cells from each time point+irradiated PBMC
Positive control:
T-cells from each time point+irradiated PBMC+1 µg/ml SEC-3.
Test sample:
T-cells from each time point+irradiated PBMC (10 µM of each peptide):
I) For bulk cultures stimulated with 13C+13R: 13C+13R mix or single G13C peptides
ID For bulk cultures stimulated with TG02+13R: TG02+13R, 13C+13R mix, or single G13C peptides
Incubate the cells for 48 hours at 37° C./5% $CO_2$.
5. Add 20 µL of $^3$H-Thymidine ($3.7\times10^4$ Bq).
6. Incubate at 37° C./5% $CO_2$ for 17 hours.
7. Harvest the cells to Unifilters using the Filtermate 196 Harvester and dry the filters at 45° C. until completely dry (normally this is achieved after 1.5 but the number of hours left at 45° C. after this is not critical, hence plates can be counted 60 hours later).
8. Cover the bottom of the Unifilters with adhesive covers (delivered with the Unifilters) and add 25 µl micro scintillation liquid to each well. Cover the plate with TopSeal and place the filters in a TopCount Packard microplate scintillation beta counter. Enter assay wizard program. Select protocol/program $^3$H Thymidine in triplicates. Enter report definition and ASCII file output. Under directory, select data folder (each user should have a separate folder). Choose name for experiment file to save. Stacker on or off (use stacker if more than one plate). Start the assay program.

ii) Second Stimulation of Bulk Cultures

The remaining cells (1-2×106 T cells/well) were re-stimulated once more with autologous PBMCs (1 mill/well) and peptide mixes (as described in step b.).

TABLE 8

Stimulation - Numbers of wells stimulated with the peptide mixes

| | Peptide mix: 13C + 13R | Peptide mix: 13R + TG02-mix |
|---|---|---|
| Buffy 1 | 1 | 1 |
| Buffy 2 | 2 | 2 |
| Buffy 3 | 3 | 3 |
| Buffy 4 | 3 | 1 |

1. Culture the cells in a humidified incubator at 37° C./5% $CO_2$ for 3 days (as described in step b.).
2. Day 17: Add a final concentration of 40 iU/ml of recombinant human interleukin-2 and final concentration of 5 ng/ml recombinant human IL-7 to the cell cultures and continue incubation at 37° C./5% $CO_2$. Cells are checked regularly under the microscope and split when required.
3. Day 19-21: 500 μl was withdrawn from each well and replaced with 500 μl fresh CellGro DC medium, supplemented with 40 iU/ml IL-2 and IL-7.
4. Day 22-27: Cells were checked regularly each day, and wells with slow growing T cells were mixed together (as in step b.).

d. i) 3-Days Cell Proliferation Assay
1. Harvest, wash and count T cells in the bulk cultures.

TABLE 9

Total cell number

| | Peptide mix: 13C + 13R | Peptide mix: 13R + TG02-mix |
|---|---|---|
| Buffy 1 | 0.09 × 10$^6$ | 0.18 × 10$^6$ |
| Buffy 2 | 4.5 × 10$^6$ | 5.4 × 10$^6$ |
| Buffy 3 | 2.7 × 10$^6$ | 3.15 × 10$^6$ |
| Buffy 4 | 1.35 × 10$^6$ | 1.76 × 10$^6$ |

2. Transfer 5×10$^4$ T cells from bulk cultures per well in round-bottomed 96-well plates.
3. Thaw 1 vial of autologous PBMCs sample in CellGro DC medium. Irradiate PBMCs (30 Gy), count and add 5×10$^4$ cells to each well and adjusted to a total volume of 200 μl/well with DC medium (as described in step c.i)).

ii) Day 27-42: Third Stimulation of Bulk Cultures

The remaining cells (1-2 mill T cells/well) were re-stimulated once more with autologous PBMs (1 mill/well) and peptide mix (as described in step b.)

TABLE 10

Stimulation - Numbers of wells stimulated

| | Peptidemix: 13C + 13R | Peptide mix: 13R + TG02-mix |
|---|---|---|
| Buffy 1 | 0 | 0 |
| Buffy 2 | 2 | 2 |

TABLE 10-continued

Stimulation - Numbers of wells stimulated

| | Peptidemix: 13C + 13R | Peptide mix: 13R + TG02-mix |
|---|---|---|
| Buffy 3 | 1 | 1 |
| Buffy 4 | 1 | 1 | e) 3-Days T Cell Proliferation Assay
1. Harvest, wash and count T cells in the bulk cultures.

TABLE 11

Total cell number

| | Peptide mix: 13C + 13R | Peptide mix: 13R + TG02-mix |
|---|---|---|
| Buffy 1 | 0 | 0 |
| Buffy 2 | 0.9 × 10$^6$ | 0.63 × 10$^6$ |
| Buffy 3 | 0.27 × 10$^6$ | 0.675 × 10$^6$ |
| Buffy 4 | 0.315 × 10$^6$ | 0.18 × 10$^6$ |

2. Transfer 5×10$^4$ T cells from bulk cultures per well into round-bottomed 96-well plates.
3. Thaw 1 vial of autologous PBMCs sample in CellGro DC medium. Irradiate PBMCs (30 Gy), count and 5×10$^4$ cells were added to each well and adjusted to a total volume of 200 μl/well with DC medium (as described in step c.i)).

Results

The results of the T cell proliferation assays with the peptide mixtures, following three rounds of stimulation of the bulk cultures, are shown in Tables 12-14, and FIGS. 6-8, respectively. Tables 12-14 show the counts per minute (CPM) for each replicate, and the mean CPM for each donor.

TABLE 12

Counts per minute (CPM) after stimulation with a peptide mixture consisting of 13C and 13R peptides. During the three rounds of in vitro stimulation of the bulk cultures, Donor #3 was stimulated with the TG02 + 13R peptide mixture, while Donor #4 was stimulated with the 13C + 13R peptide mixture.

| | APC | APC + T cell | APC + T cell + 13C + 13R |
|---|---|---|---|
| Donor #3 | 337 | 8337 | 28,422 |
| | 235 | 12,061 | 28,264 |
| | 375 | n/a | n/a |
| Mean Donor #3 | 316 | 10,199 | 28,343 |
| Donor #4 | 137 | 9696 | 32,476 |
| | 421 | 8412 | 23,499 |
| | 249 | n/a | n/a |
| Mean Donor #4 | 269 | 9054 | 27,987 |

TABLE 13

Counts per minute (CPM) after stimulation with a peptide mixture consisting of 13C, 13D, 12A, 12C, 12D, 12R, 12S, 12V and 13R (i.e. TG02 + 13R) peptides. During the three rounds of in vitro stimulation of the bulk cultures, Donor #3 was stimulated with the TG02 + 13R peptide mixture.

| | APC | APC + T cell | APC + T cell + 13R + TG02 |
|---|---|---|---|
| Donor #3 | 337 | 4954 | 28,796 |
| | 235 | 6073 | 21,201 |
| | 375 | 5513 | n/a |
| Mean Donor #3 | 316 | 5513 | 24,998 |

TABLE 14

Counts per minute (CPM) after stimulation with a 13C peptide. During the three rounds of in vitro stimulation of the bulk cultures, Donor #3 was stimulated with the TG02 + 13R peptide mixture.

|  | APC | APC + T cell | APC + T cell + 13C |
|---|---|---|---|
| Donor #3 | 337 | 4954 | 27813 |
|  | 235 | 6073 | 32522 |
|  | 375 | 5513 | 28869 |
| Mean Donor #3 | 316 | 5513 | 29735 |

The results of the positive control were confirmed but are not included in FIGS. 6-8 for scaling reasons. As can be seen, both of the peptide mixtures and the single peptide induced T cell proliferation, indicating that the peptide and peptide mixtures were able to induce an immune response in humans.

Example 2

In this Example, mice were repeatedly vaccinated subcutaneously with TG02, in order to analyse the immune response. Following the vaccination, splenocytes were harvested, and the proliferative response of the splenocytes was measured. The results are shown in FIG. 9.

Method

Characterisation of the Test Item
Name: TG02
Product: TG02 consists of equal amounts (weight) of 8 different peptides (12A, 12C, 12D, 12R, 12S, 12V, 13C, 13D)
Batch No.: 12A: lot no 1034804; 12C: lot no 1034803; 12D: lot no 1034801; 12R: lot no 1034802; 12S: lot no 1034805; 12V: lot no 1034800; 13C: lot no 1050468; 13D: lot no 1034806
Therapeutic Indication: cancer
Physical State: powder
Colour: white
Purity: 80 mg net peptide per vial (10 mg net of each peptide)
Storage Conditions: −15° C.−−20° C. and protected from light
Expiry Date: 31 Dec. 2014
Safety Precautions: Routine hygienic procedures were sufficient to assure personnel health and safety.
Characterisation on of the Vehicle 1
Name: ViscoGel
Batch No.: VG14056
Therapeutic Indication: cancer
Physical State: gel particles
Colour: colourless
Water Content: 99%
Storage Conditions: 2-8° C.
Expiry Date: 1 Jun. 2015
Safety Precautions: The routine hygienic procedures will be sufficient to assure personnel health and safety.
Characterisation on of the Vehicle 2
The vehicle 2 to be used in this study will be aqua ad injectionem. The specifications provided by the supplier are listed as follows:
Name: aqua ad injectionem
Physical State: liquid
Storage Conditions: room temperature
Safety Precautions: Routine hygienic procedures were sufficient to assure personnel health and safety.

Preparation of the Test Item
5 ml aqua ad injectionem was added to one vial TG02 (80 mg) and was gently swirled (avoid foaming) to obtain a homogenous stock solution of 16 mg TG02 per mL
For animals of group 1 (see Table 12), 1 mL TG02 stock solution was extracted with a syringe and mixed with 1 mL aqua ad injectionem to obtain a final concentration of 8 mg/mL.
For animals of the groups 2 and 3 (see Table 12), 1 ml TG02 stock solution was extracted with a syringe and mixed with 1 mL ViscoGel™ to obtain a final concentration of 8 mg/mL.
Test item formulations were considered to be stable for 6 h at 2-8° C.
Test System
Species/strain: healthy BALB/c mice (full barrier) BALB/cAnNCrl
Source: Charles River, 97633 Sulzfeld, Germany
Sex: female
Age at the start of the treatment period: approximately 6-8 weeks old
Number of animals: 30 (10 animals per group)
The animals were derived from a controlled full-barrier maintained breeding system (SPF). According to Art. 9.2, No. 7 of the German Act on Animal Welfare, the animals were bred for experimental purposes.
Housing and Feeding Conditions
Full barrier in an air-conditioned room.
Temperature: 22±3° C.
Relative humidity: 55±10%.
Artificial light, sequence being 12 hours light, 12 hours dark.
Air change: 10x/hour.
Free access to Altromin 1324 maintenance diet for rats and mice.
Free access to tap water, sulphur acidified to a pH of approximately 2.8 (drinking water, municipal residue control, microbiological controls at regular intervals).
The animals will be kept in groups of 5 animals per cage in IVC cages, type II L, polysulphone cages on Altromin saw fibre bedding.
Certificates of food, water and bedding are filed at BSL BIOSERVICE.
Adequate acclimatisation period (at least 5 days) under laboratory conditions.
Allocation and Identification of the Animals
Animals showing pathological signs before administration were excluded from the study. Supplementary animals from the same delivery were provided in exchange. Each animal was marked for individual identification with an ear mark.
Experimental Procedure
The study was conducted with 3 groups, each compromising 10 female BALB/c mice. The start of the study was performed on two separate days on which 5 of the animals per group were treated. Therefore the groups were divided into part I and part IL The animals were treated subcutaneously at different time points (Table 12).
During the period of administration, the animals were observed precisely each day for signs of toxicity. 48 hours after the last administration the animals were euthanised, examined macroscopically and the spleen was prepared for further analysis.
Dosage
In all groups the test item was administered at repeated time points (Table 15) by subcutaneous injection between the nape of the neck and the shoulder. The application volume for all groups was 0.1 mL (0.80 mg TG02).

TABLE 15

Treatment and Animal Identification

| Group | Treatment | Animal No. Part I | Animal No. Part II | Time Points of Subcutaneous Application (Day) | Subjected to Necropsy (hours after last administration) |
|---|---|---|---|---|---|
| 1 | TG02 | 1-5 | 6-10 | 1, 8, 15, 22 | 48 |
| 2 | TG02 + ViscoGel ™ | 11-15 | 16-20 | 1, 8, 15, 22 | 48 |
| 3 | TG02 + ViscoGel ™ | 21-25 | 26-30 | 1, 22 | 48 |

Clinical Observations

All animals were observed for clinical signs during the entire treatment period of 24 days.

General clinical observations were made at least once a day, preferably at the same time each day and considering the peak period of anticipated effects after dosing. The health condition of the animals was recorded.

On each of the animals, general clinical observations including changes in the skin and fur, eyes and mucous membranes were performed preferably at the same time each day and considering the peak period of anticipated effects after dosing. Also respiratory, circulatory, autonomic and central nervous systems and somatomotor activity and behaviour pattern were examined. Particular attention was directed to observations of signs of anaphylactoid reactions, paralysis, tremor, convulsions, salivation, diarrhoea, lethargy, sleep and coma. Moreover, attention was directed to the injection site.

Pathology-Gross Necropsy 48 hours after the last administration (study day 24) animals were sacrificed by cervical dislocation and were subjected to a detailed gross necropsy which includes careful examination of the external surface of the body, all orifices and the cranial, thoracic and abdominal cavities and their contents.

Cell Culture and Stimulation of Splenic Cells

The spleen of all animals was removed, transferred to cell culture medium (RPMI 1640 medium supplemented with 10% FCS, 100 U/mL Penicillin, 100 µg/mL Streptomycin, 2 mM L-Glutamine, and 50 µM beta-mercaptoethanol) and stored on ice. All steps were performed sterile and cells were kept on ice.

A single cell suspension from splenic cells was generated using a cell strainer. After centrifugation (350 g, 5 min, 5±3° C.), supernatant was removed and the cell pellet was resuspended in ACK buffer and incubated for 5 min at RT. 10 mL cell culture medium was added. The samples were left 5 min on bench top to let the cell debris sediment. The suspension above the cell debris was transferred into another tube and was centrifuged (350 g, 5 min, 5±3° C.). The supernatant was removed and the cell pellet was resuspended in 10 mL cell culture medium. After counting of cells, 0.2 Mio cells were seeded in a 96 well plate (180 µL per well; $1,1*10^6$ cells/mL). 9 replicates were plated on each plate for each spleen.

(1) 1 plate for harvesting of supernatant for cytokine measurement after 24 h (results not shown)
(2) 1 plate for harvesting of supernatant for cytokine measurement after 48 h (results not shown)
(3) 1 plate for the proliferation assay The following stimulations were performed:
3 replicates: unstimulated (addition of 20 µL cell culture medium)
3 replicates: stimulation with 10 µM TG02 (8 peptides, 10 µM end concentration per peptide, addition in 20 µL cell culture medium)
3 replicates: stimulation with 1 µg/200 µL, ConA (Concanavalin A) (addition of 1 µg ConA in 20 µL cell culture medium)

Incubation at 37° C. and 5% $CO_2$ for 24 h (1), 48 h (2) or 5 days (3).

The remaining cells were centrifuged (350 g, 5 min, 5±3° C.), transferred to a 1.5 mL tube, centrifuged again (350 g, 5 min, 5±3° C.), the supernatants were completely removed and the cell pellets were frozen at ≤−70° C.

(1) After 24 h, the corresponding plates were centrifuged (350 g, RT) and 150 µL of the supernatant were harvested and frozen at ≤−70° C.

(2) After 48 h, the corresponding plates were centrifuged (350 g, RT) and 150 µL of the supernatant were harvested and frozen at ≤−70° C.

Proliferation Assay (3) After 5 days, 1 µCi/well $^3$H-Thymidine was added to the samples, which were then incubated for 18 h at 37° C. and 5% $CO_2$. The plates were then frozen at ≤−20° C.

Plates were thawed at RT. After washing off the harvester, the samples were transferred to a filter plate using the harvester followed by 5 washing steps using water. Filter plates were dried at RT overnight. A foil was stuck to the bottom of the filter plates and 20 µL scintillation fluid was added to the wells. After incubation of 1 h at RT, the samples were measured using a TopCount NXT and the stimulation index (SI) was calculated. SI=CPM of stimulated samples/CPM of control samples.

Results

Table 16 and FIG. 9 show the results of the splenocyte proliferation assay. Table 16 shows the CPM for each replicate, and the mean CPM for each mouse. As can be seen, splenocytes stimulated with TG02 showed an increased CPM as compared to unstimulated splenocytes, indicating that TG02 induced an immune response.

TABLE 16

Counts per minute (CPM) after stimulation with TG02.

|  | Splenocytes | Splenocytes + TG02 | Splenocytes + ConA |
|---|---|---|---|
| Mouse #4 | 12825 | 7772 | 15,113 |
|  | 2540 | 10,038 | 12,612 |
|  | 2729 | 5313 | 17,906 |
| Mean Mouse #4 | 2635 | 7708 | 15,210 |
| Mouse #7 | 1541 | 3999 | 5305 |
|  | 2116 | 1734 | 6252 |
|  | 378 | 2721 | 6916 |
| Mean Mouse #7 | 1345 | 2818 | 6158 |
| Mouse #24 | 3061 | 11,673 | 7834 |
|  | 2805 | 9547 | 8578 |
|  | 2580 | 11,338 | 10,057 |
| Mean Mouse #24 | 2815 | 10,853 | 8823 |
| Mouse #29 | 1183 | 4616 | 9480 |
|  | 8133 | 4840 | 13,292 |
|  | 1573 | 1990 | 10,033 |
| Mean Mouse #29 | 1728 | 4728 | 10,935 |
| Mouse #30 | 12,136 | 9787 | 32,205 |
|  | 3204 | 26,083 | 35,668 |
|  | 4189 | 18,800 | 42,149 |
| Mouse #30 | 6510 | 18,223 | 36,687 |

What is claimed is:

1. A T-cell mixture, suitable for administration to a patient,
    wherein the T-cell mixture comprises T-cells specific for:
    a peptide consisting of the amino acid sequence of SEQ ID NO: 19 when presented on an MHC molecule,
    a peptide consisting of the amino acid sequence of SEQ ID NO: 20 when presented on an MHC molecule,
    a peptide consisting of the amino acid sequence of SEQ ID NO: 21 when presented on an MHC molecule,
    a peptide consisting of the amino acid sequence of SEQ ID NO: 22 when presented on an MHC molecule,
    a peptide consisting of the amino acid sequence of SEQ ID NO: 23 when presented on an MHC molecule,
    a peptide consisting of the amino acid sequence of SEQ ID NO: 24 when presented on an MHC molecule,
    a peptide consisting of the amino acid sequence of SEQ ID NO: 25 when presented on an MHC molecule, and
    a peptide consisting of the amino acid sequence of SEQ ID NO: 26 when presented on an MHC molecule.

2. A T-cell mixture, suitable for administration to a patient,
    wherein the T-cell mixture comprises T-cells specific for:
    a peptide consisting of the amino acid sequence of SEQ ID NO: 27 when presented on an MHC molecule,
    a peptide consisting of the amino acid sequence of SEQ ID NO: 28 when presented on an MHC molecule,
    a peptide consisting of the amino acid sequence of SEQ ID NO: 29 when presented on an MHC molecule,
    a peptide consisting of the amino acid sequence of SEQ ID NO: 30 when presented on an MHC molecule,
    a peptide consisting of the amino acid sequence of SEQ ID NO: 31 when presented on an MHC molecule, and
    a peptide consisting of the amino acid sequence of SEQ ID NO: 32 when presented on an MHC molecule.

3. A pharmaceutical composition comprising a T-cell mixture according to claim 1, and a pharmaceutically-acceptable carrier, diluent and/or excipient.

4. A method of stimulating the immune system in a human patient with cancer, wherein the cancer is associated with RAS protein amino acid substitutions, the method comprising:
    i) selecting a T-cell mixture according to claim 1; and
    ii) administering the T-cell mixture to the patient.

5. A pharmaceutical composition comprising a T-cell mixture according to claim 2, and a pharmaceutically-acceptable carrier, diluent and/or excipient.

6. A method of stimulating the immune system in a human patient with cancer, wherein the cancer is associated with RAS protein amino acid substitutions, the method comprising:
    i) selecting a T-cell mixture according to claim 2; and
    ii) administering the T-cell mixture to the patient.

* * * * *